(12) United States Patent
Cover et al.

(10) Patent No.: US 6,652,488 B1
(45) Date of Patent: Nov. 25, 2003

(54) SURGICAL SUCTION IRRIGATOR

(75) Inventors: Reid Cover, Mountain View, CA (US); Thomas Martin Keast, Mountain View, CA (US); Anthony Chikuo Lee, Mountain View, CA (US); Sean Barry Cahill, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 238 days.

(21) Appl. No.: 09/659,466

(22) Filed: Sep. 11, 2000

(51) Int. Cl.$^7$ ................................................. A61M 1/00
(52) U.S. Cl. ......................................... 604/118; 604/32
(58) Field of Search ................................. 604/118, 119, 604/21, 27, 30, 31, 32, 33, 34, 35, 43

(56) References Cited

U.S. PATENT DOCUMENTS

| | | |
|---|---|---|
| 1,846,596 A | 2/1932 | Hertzberg |
| 2,112,629 A | 3/1938 | Lloyd |
| 2,197,995 A | 4/1940 | Crowley |
| 2,243,285 A | 5/1941 | Pope |
| 2,733,713 A | 2/1956 | Kabnick |
| 3,001,288 A | 9/1961 | Freedman |
| 3,065,749 A | 11/1962 | Brass |
| 3,208,145 A | 9/1965 | Turner |
| 3,227,158 A | 1/1966 | Mattingly |
| 3,237,306 A | 3/1966 | Staunt |
| 3,353,537 A | 11/1967 | Knox et al. |
| 3,426,743 A | 2/1969 | Chesnut et al. |
| 3,515,130 A | 6/1970 | Tsujino |
| 3,561,433 A | 2/1971 | Kovach |
| 3,653,377 A | 4/1972 | Rebold |
| 3,731,676 A | 5/1973 | Rebold |
| 3,749,090 A | 7/1973 | Stewart |
| 3,762,411 A | 10/1973 | Lloyd et al. |
| 3,768,472 A | 10/1973 | Hodosh et al. |
| 3,794,031 A | 2/1974 | Bloom |
| 3,861,383 A | 1/1975 | Kovach |
| 3,883,074 A | 5/1975 | Lambert |
| 3,889,675 A | 6/1975 | Stewart |
| 3,949,753 A | 4/1976 | Dockhorn |

(List continued on next page.)

FOREIGN PATENT DOCUMENTS

| | | |
|---|---|---|
| GB | 2 063 674 A | 6/1981 |
| WO | WO85/03982 | 9/1985 |
| WO | WO86/04247 | 7/1986 |
| WO | WO91/12830 | 9/1991 |
| WO | WO93/17733 | 9/1993 |
| WO | WO94/13335 | 6/1994 |
| WO | WO94/19030 | 9/1994 |
| WO | WO94/23773 | 10/1994 |

OTHER PUBLICATIONS

KLI DeCherney Hysteroscopy Pump believed published before Apr. 19, 1993.

(List continued on next page.)

Primary Examiner—Harry B. Tanner
(74) Attorney, Agent, or Firm—Flynn, Thiel, Boutell & Tanis, P.C.

(57) ABSTRACT

A surgical fluid flow handpiece provides a range of relatively low flow rates with relatively fine manual control in selecting a flow rate in such relatively low range, and also provides for manual selection of a relatively high flow rate namely a flow rate well above such range. The handpiece is shaped to complement the shape of a user's hand.

42 Claims, 29 Drawing Sheets

U.S. PATENT DOCUMENTS

| | | |
|---|---|---|
| 3,993,054 A | 11/1976 | Newman |
| 4,007,739 A | 2/1977 | Bron et al. |
| 4,030,495 A | 6/1977 | Virag |
| 4,030,498 A | 6/1977 | Tompkins |
| 4,099,527 A | 7/1978 | Howell .................. 128/214 C |
| 4,215,476 A | 8/1980 | Armstrong |
| 4,248,589 A | 2/1981 | Lewis |
| 4,275,726 A | 6/1981 | Schael |
| 4,276,023 A | 6/1981 | Phillips et al. |
| 4,278,078 A | 7/1981 | Smith |
| 4,282,867 A | 8/1981 | Du Toit |
| 4,424,055 A | 1/1984 | Herman |
| 4,428,748 A | 1/1984 | Peyman et al. |
| 4,460,358 A | 7/1984 | Somerville et al. |
| 4,468,221 A | 8/1984 | Mayfield |
| 4,482,345 A | 11/1984 | Chow et al. |
| 4,489,750 A | 12/1984 | Nehring |
| 4,493,694 A | 1/1985 | Wuchinich |
| 4,508,532 A | 4/1985 | Drews et al. |
| 4,509,507 A | 4/1985 | Yabe |
| 4,519,385 A | 5/1985 | Atkinson et al. |
| 4,526,573 A | 7/1985 | Lester et al. |
| 4,534,758 A | 8/1985 | Akers et al. |
| 4,535,773 A | 8/1985 | Yoon |
| 4,537,182 A | 8/1985 | Otani |
| 4,537,209 A | 8/1985 | Sasa |
| 4,552,130 A | 11/1985 | Kinoshita |
| 4,561,431 A | 12/1985 | Atkinson |
| 4,583,531 A | 4/1986 | Mattchen |
| 4,604,089 A | 8/1986 | Santangelo et al. |
| 4,621,770 A | 11/1986 | Sayen |
| 4,634,420 A | 1/1987 | Spinosa et al. |
| 4,635,621 A | 1/1987 | Atkinson |
| 4,647,738 A | 3/1987 | Diamond .................. 200/81 H |
| 4,655,197 A | 4/1987 | Atkinson |
| 4,655,754 A | 4/1987 | Richmond et al. |
| 4,662,829 A | 5/1987 | Nehring |
| 4,667,655 A | 5/1987 | Ogiu et al. |
| 4,696,669 A | 9/1987 | Menhusen |
| 4,705,500 A | 11/1987 | Reimels et al. |
| 4,741,678 A | 5/1988 | Nehring |
| 4,748,970 A | 6/1988 | Nakajima |
| 4,759,349 A | 7/1988 | Betz et al. |
| 4,764,165 A | 8/1988 | Reimels et al. |
| 4,765,588 A | 8/1988 | Atkinson ................. 251/149.1 |
| 4,776,840 A | 10/1988 | Freitas et al. |
| 4,817,599 A | 4/1989 | Drews |
| 4,857,068 A | 8/1989 | Kahn ........................ 604/405 |
| 4,872,837 A | 10/1989 | Issalene et al. |
| 4,935,005 A | 6/1990 | Haines |
| 4,941,872 A | 7/1990 | Felix et al. |
| 4,957,483 A | 9/1990 | Gonser et al. |
| 4,982,739 A | 1/1991 | Hemstreet et al. |
| 5,019,038 A | 5/1991 | Linden |
| 5,037,431 A | 8/1991 | Summers et al. |
| 5,046,486 A | 9/1991 | Grulke et al. |
| 5,053,002 A | 10/1991 | Barlow |
| 5,054,947 A | 10/1991 | Frank et al. ................ 401/146 |
| 5,057,015 A | 10/1991 | Fleer |
| 5,098,387 A | 3/1992 | Wiest et al. |
| 5,098,405 A | 3/1992 | Peterson et al. ............ 604/247 |
| 5,100,058 A | 3/1992 | Wei |
| 5,120,305 A | 6/1992 | Boehringer et al. |
| 5,142,723 A | 9/1992 | Lustig et al. |
| 5,147,292 A | 9/1992 | Kullas et al. |
| 5,170,779 A | 12/1992 | Ginsberg |
| 5,176,629 A | 1/1993 | Kullas et al. |
| 5,186,714 A | 2/1993 | Boudreault et al. |
| 5,188,591 A | 2/1993 | Dorsey, III |
| 5,195,958 A | 3/1993 | Phillips ...................... 604/33 |
| 5,195,959 A | 3/1993 | Smith |
| 5,197,460 A | 3/1993 | Ito et al. |
| 5,203,769 A | 4/1993 | Clement et al. |
| 5,224,929 A | 7/1993 | Remiszewski |
| 5,244,459 A | 9/1993 | Hill ............................ 604/33 |
| 5,261,905 A | 11/1993 | Doresey, III |
| 5,269,750 A | 12/1993 | Grulke et al. |
| 5,281,214 A | 1/1994 | Wilkins et al. |
| 5,295,956 A | 3/1994 | Bales et al. |
| 5,303,735 A | 4/1994 | Cerola et al. |
| 5,322,503 A | 6/1994 | Desai |
| 5,322,506 A | 6/1994 | Kullas ........................ 604/30 |
| 5,333,603 A | 8/1994 | Schuman |
| 5,334,140 A | 8/1994 | Phillips ....................... 604/35 |
| 5,348,555 A | 9/1994 | Zinnanti ...................... 604/33 |
| 5,380,277 A | 1/1995 | Phillips ....................... 604/33 |
| 5,388,612 A | 2/1995 | Cerola et al. ............ 137/596.2 |
| 5,391,145 A | 2/1995 | Dorsey, III |
| 5,447,494 A | 9/1995 | Dorsey, III .................. 604/43 |
| 5,449,357 A | 9/1995 | Zinnanti ...................... 604/33 |
| 5,470,305 A | 11/1995 | Arnett et al. |
| 5,484,402 A | 1/1996 | Saravia et al. |
| 5,514,089 A | 5/1996 | Walbrink et al. ............. 604/33 |
| 5,522,796 A | 6/1996 | Dorsey, III |
| 5,562,640 A | 10/1996 | McCabe et al. |
| 5,573,504 A | 11/1996 | Dorsey, III .................. 604/35 |
| 5,578,000 A | 11/1996 | Greff et al. ................... 604/22 |
| 5,586,977 A | 12/1996 | Dorsey, III ................. 604/264 |
| 5,607,391 A | 3/1997 | Klinger, III .................. 604/33 |
| 5,609,573 A | 3/1997 | Sandock ...................... 604/22 |
| 5,707,351 A | 1/1998 | Dorsey, III .................. 604/30 |
| 5,792,098 A | 8/1998 | Felix et al. ................... 604/27 |
| 5,792,108 A | 8/1998 | Felix et al. ................. 604/131 |
| 5,807,313 A | 9/1998 | Delk et al. ................... 604/35 |
| 5,827,218 A | 10/1998 | Nguyen et al. .............. 604/30 |
| 6,022,329 A | 2/2000 | Arnett et al. |
| 6,059,754 A | 5/2000 | Pasch et al. ................ 604/152 |
| 6,099,494 A | 8/2000 | Henniges et al. ............. 604/35 |
| 6,156,004 A | 12/2000 | Tremaine et al. ............. 604/27 |
| 6,162,194 A | 12/2000 | Shipp ........................ 604/151 |
| 6,176,847 B1 | 1/2001 | Humphreys, Jr. et al. .. 604/246 |
| 6,200,292 B1 | 3/2001 | French et al. ............... 604/131 |
| 6,213,970 B1 | 4/2001 | Nelson et al. |
| 6,352,527 B1 | 3/2002 | Henniges et al. ........... 604/351 |
| 6,371,934 B1 | 4/2002 | Jackson et al. ............... 604/35 |
| 6,394,996 B1 | 5/2002 | Lawrence et al. .......... 604/540 |
| 6,485,452 B1 | 11/2002 | French et al. ................ 604/39 |

OTHER PUBLICATIONS

Marlow—Unique Products for Advanced Operative Laparoscopy 790—5M.

Select One™Minimal Access Surgery System, Introducing the VAC—™Handcontrolled Suction Irrigation Instrument, ConMed Aspen Surgical Systems, Conmed 7/92, 10M.

Select One—™Minimal Access Surgery System, The Modular Instrument System for Surgical Endoscopy, SelectOne System, by ConMed, Aspen Surgical Systems believed published before Apr. 19, 1993.

DAVOL—Endo–Flo™Irrigator, Bard, Davol Inc.; instruction booklet #041002–0, 9011R, Nov., 1990.

Count on Us (Introducing Over 100 Precision Crafted Quality Endosurgery Instruments), Davis+Geck, 1993.

Essar®Suction Irrigator, Why do I need the *Essar* Suction Irrigator? Stewart Research, Inc. believed published before Apr. 19, 1993.

"Simultaneous pulsatile lavage and/or irrigation with suction . . . ", Pulsatile Lavage Debridement System, brochure No. 82–010–5150–0146/2.5M CISS Zimmer, Inc., Snyder Labs Inc, 1982.

Nezhat–Dorsey™Hydro–Dissection™Information Booklet Installation/Operating Instructions for "Quick–Disconnect" Probe Tips (2 sheets) believed published before Apr. 19, 1993.

Suction/Irrigation Is No Longer An Issue, Hydro–Dissection System, 556529 PP ICM 7/92, Karl Stroz Gmbh & Co. Tuttlengen, West Germany.

A Fully Integrated Laparoscopic Irrigation and Instrumentation System, Cabot Medical, Langhorne, PA 4/92, 10M, L/T (4 sheets).

Advances In Pelviscopy, The Irrigation Pump System, Cabot Medical, Langhorne, PA 4/90 (3 sheets).

InteliJET™, Fluid Management System User's Manual, Smith & Nephew Dyonics Inc., copyright 1992, PN1060170.

Davol, Arthro–Flo®, Instructions For Use, 038657–0 901R C.R. Bard, Inc. Cranston RI, Jan. , 1990.

Davol, Arthro–Flo High–Flo Irrigator, Bard, OP–AF0015000 8/92 5M C.R. Bard Inc. Cranston, RI.

3M Fluid Control System, For Precise Control of all Arthroscopic Procedures, 70–2008–5458–9, 1992 3M.

Davol, Instructions for Use, Simpulse—™Suction/Irrigator, BARD, 034089–0 (2 sheets) Jan., 1985.

"Introducing the multi–functional instrument for virtually every laparoscopic case", USSC, Auto Suture Company, Copyright 1992, 556529 PP, 10M 7/92.

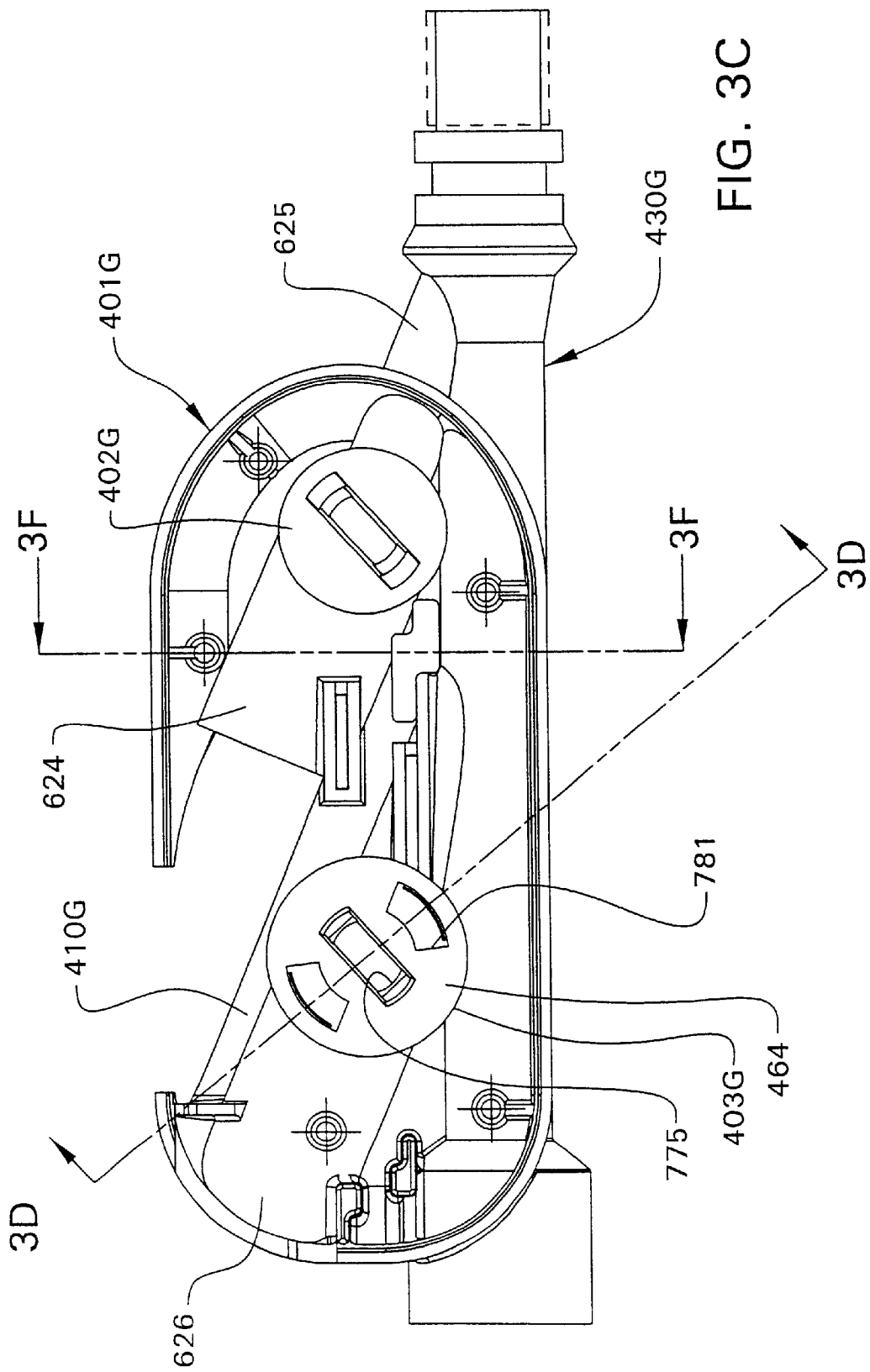

closed position, valve closed — Notice the position of the leak actuator

Notice the position of the leak actuator leak actuator in open position, valve closed

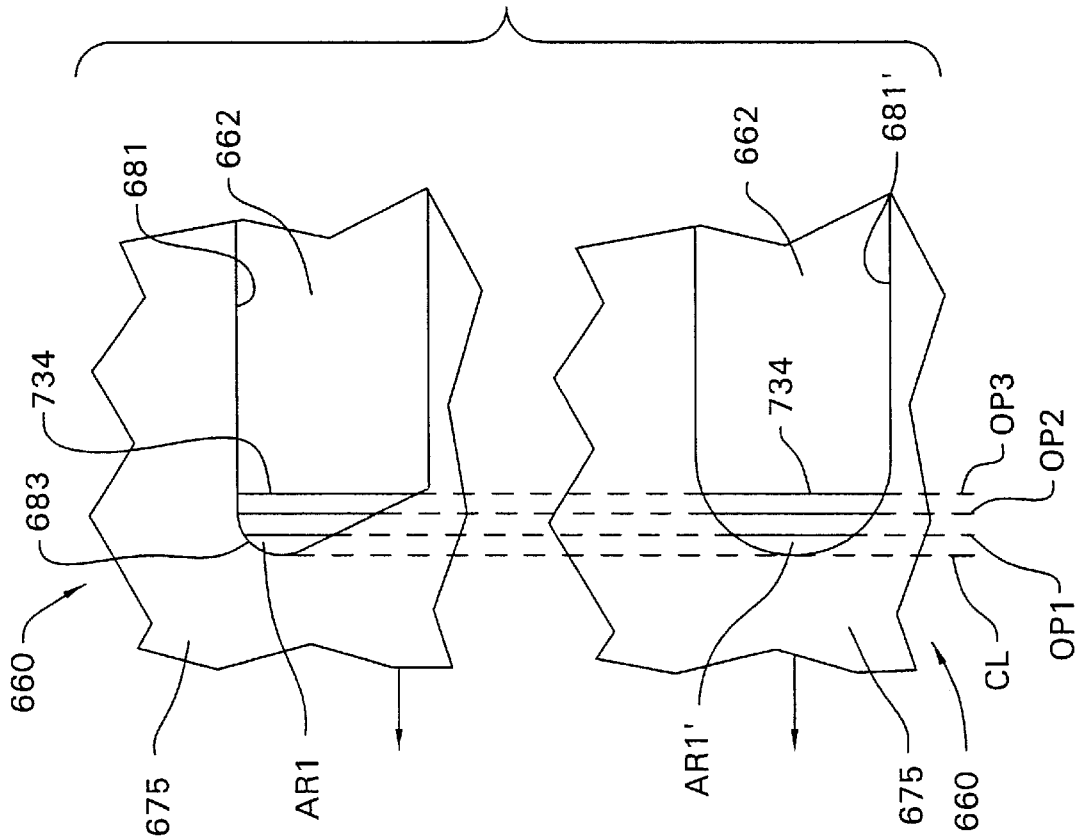

Valve Open

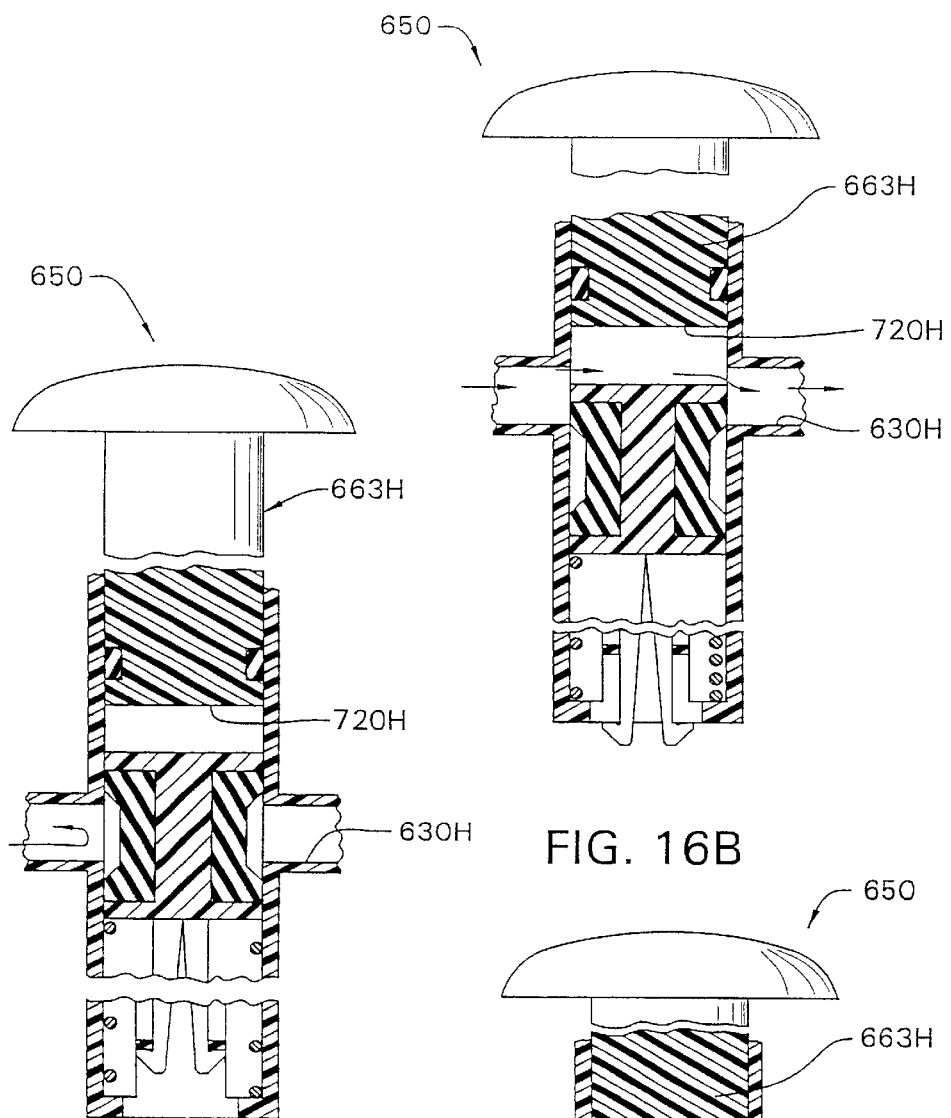
FIG. 16A
FIG. 16B
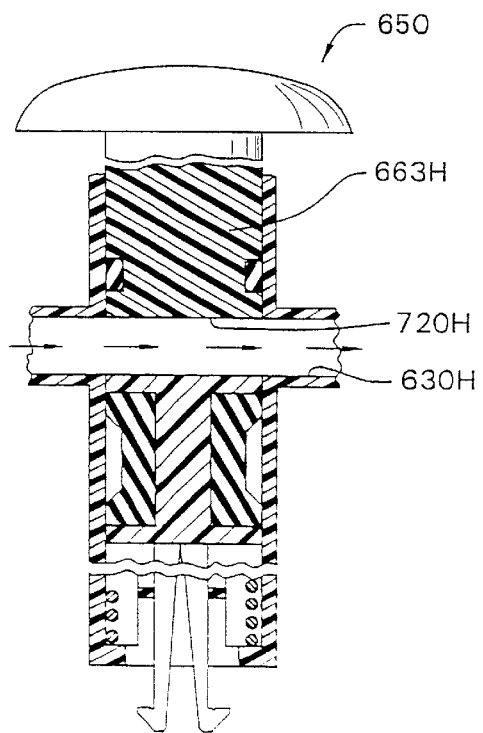
FIG. 16C

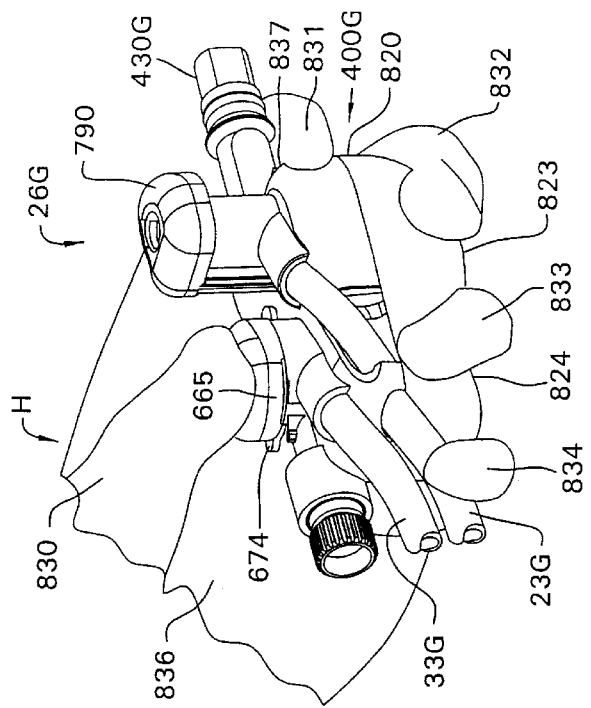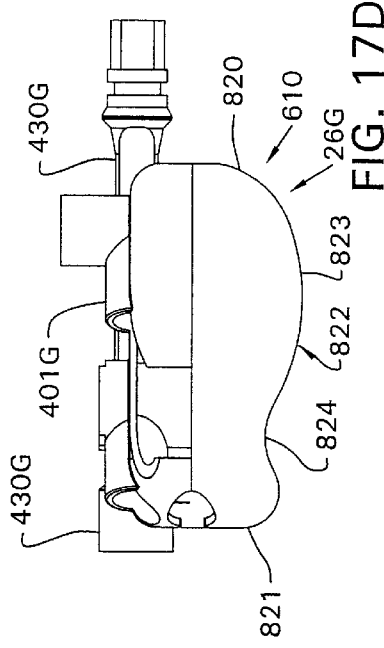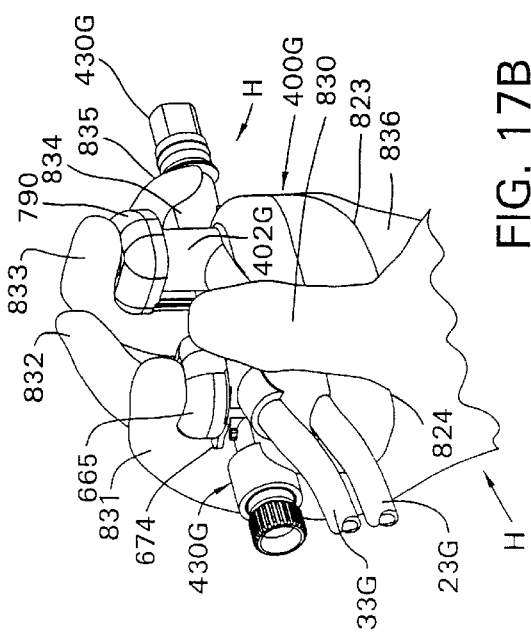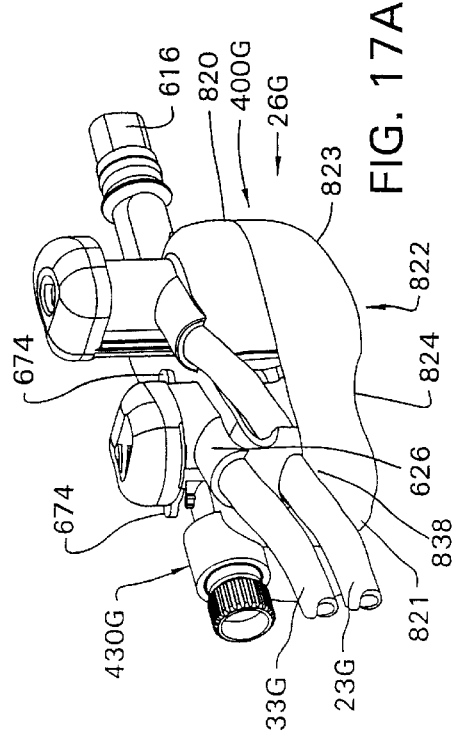

SURGICAL SUCTION IRRIGATOR

FIELD OF THE INVENTION

This invention relates to a surgical suction and irrigation system, and more particularly to one adaptable to use in endoscopic surgery.

BACKGROUND OF THE INVENTION

U.S. Pat. No. 5,484,402, assigned to the Assignee of the present invention, discloses a surgical suction irrigation system suitable for endoscopic and other surgical procedures. Such system includes a remote pumping unit comprising batteries and a motor driven pump adapted for location adjacent a conventional irrigation liquid source, (such as a conventional liquid irrigation bag), and a handpiece having suction and irrigation valves and a pump motor control switch. An irrigation liquid hose and electrical conductors connect the handpiece to the irrigation liquid pumping unit. Actuation of the handpiece irrigation liquid valve opens a path therethrough from the irrigation liquid hose and simultaneously actuates the switch to energize the pump motor and pump irrigation liquid from the irrigation liquid bag therethrough and through the handpiece to supply a surgical site.

In a continuing effort to improve on surgical suction irrigation systems, particularly endoscopic suction irrigation systems, the present invention has been developed.

Further objects and purposes of the present invention will be apparent to persons acquainted with apparatus of this general kind upon reading the following description and inspecting the accompanying drawings.

SUMMARY OF THE INVENTION

In an embodiment of the invention, a surgical fluid flow handpiece provides a range of relatively low flow rates with relatively fine manual control in selecting a flow rate in such relatively low range, and also provides for manual selection of a relatively high flow rate namely a flow rate well above such range.

In an embodiment of the invention, the handpiece is shaped to complement the shape of a user's hand.

BRIEF DESCRIPTION OF THE DRAWINGS

FIG. 3C is a bottom view of the top inverted tub of the FIG. 1 handpiece.

FIG. 9D schematically illustrates the finer control of suction flow, and very low suction flow levels, provided by the indented end configuration of a window in the suction leak control sleeve of FIG. 2.

FIG. 16A is a fragmentary, schematic, central cross sectional view of the irrigation valve in its fully closed position, and substantially as taken on the line 16A—16A of FIG. 3B.

FIG. 16B is a view similar to FIG. 16A and showing the irrigation valve unit in a partially closed condition.

FIG. 16C is a view similar to FIG. 16A but showing the irrigation valve unit in its fully open position.

FIG. 17A is a pictorial view generally similar to FIG. 1 but showing the suction and irrigation tubes extending from the handpiece.

FIG. 17B is a view similar to FIG. 17A but showing the handpiece gripped by the hand of a user in one position.

FIG. 17C is a view similar to FIG. 17B but showing the handpiece gripped by the hand of the user in another position.

FIG. 17D is a side view of the assembled top and bottom tubs of the FIG. 1 handpiece showing the profile of the handpiece shell.

DETAILED DESCRIPTION

This application incorporates by reference the disclosure (e.g. specification and drawings) of copending U.S. application Ser. No. 08/769,428 filed Dec. 19, 1996 of Nelson, et al. assigned to the Assignee of the present invention, namely Stryker Corporation, same being a continuation of U.S. application Ser. No. 08/769,428, filed Dec. 19, 1996, now abandoned, in turn a continuation in part of U.S. application Ser. No. 08/176,130 filed Dec. 30, 1993, issued as U.S. Pat. No. 5,484,402 on Jan. 16, 1996.

Figure 1:
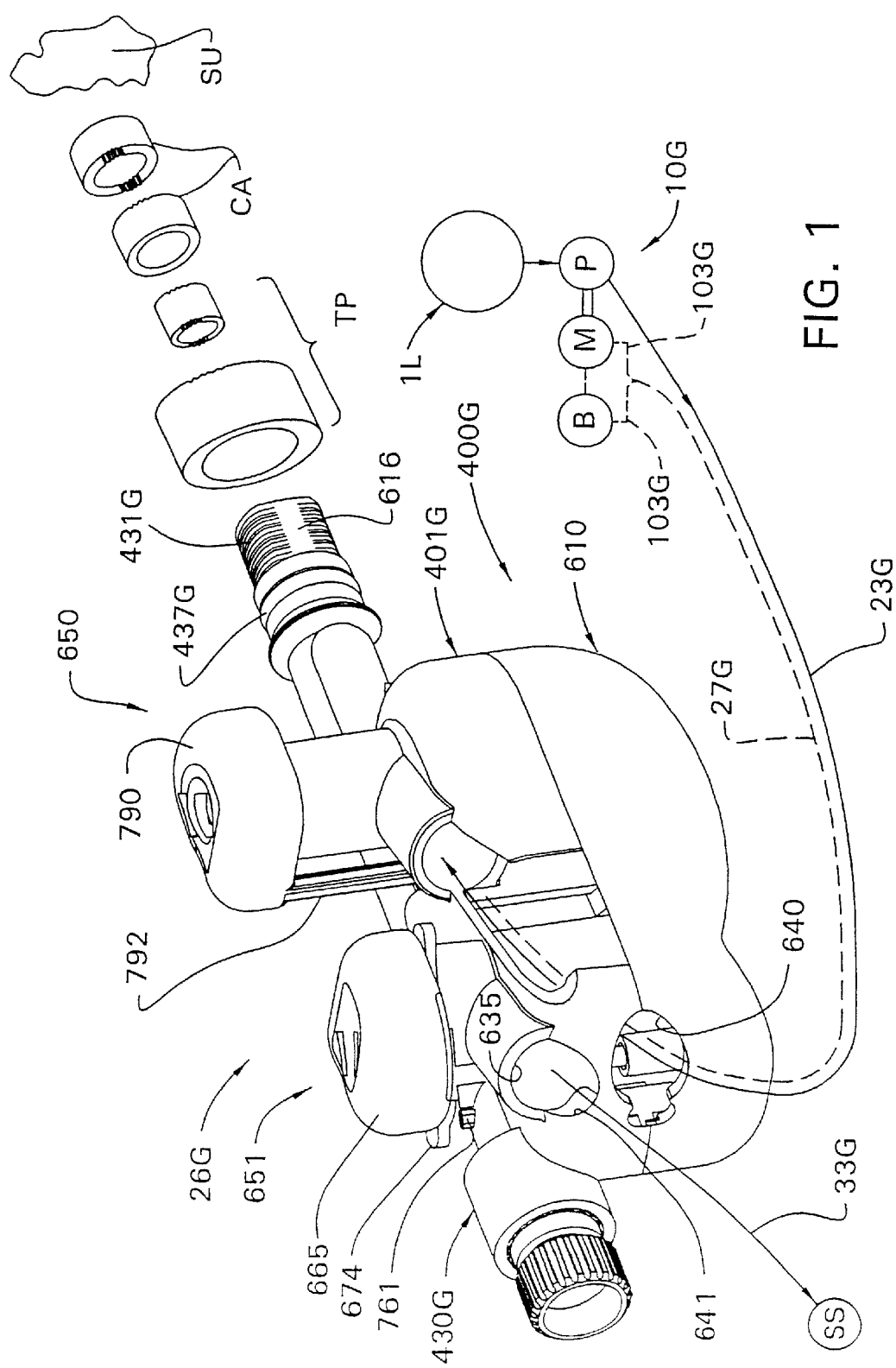
FIG. 1 is a pictorial view of a surgical handpiece embodying the invention and showing, schematically, the structure for connecting same to suction and irrigation sources as well as to a surgical site.

Turning now to the present application drawings, FIGS. 1 and onward disclose an inventive handpiece 26G. In some instances, parts of the handpiece 26G will carry the same reference numerals as generally corresponding parts of the handpiece 26D described at pages 28–48 of the above mentioned incorporated-by-reference application Ser. No. 08/769,428.

It will be understood that the inventive handpiece 26G may be used in a variety of orientations, for example in the FIG. 1 orientation, in an orientation turned upside down therefrom, or in other orientations as desired and convenient. However, for convenience in reference, in the present discussion the words "top" and "bottom", and words of similar import, shall refer to the handpiece 26G in its orientation of FIG. 1.

The components of the handpiece 26G are preferably of a suitable rigid molded plastics material, exceptions being noted below.

The handpiece 26G (FIG. 1) comprises an ergonomically rounded, easily gripped shell 400G. The shell 400G here comprises a generally downwardly opening, inverted, top tub 401G (FIG. 2), the bottom of which is fixedly closed by an upward opening bottom tub 610. The tubs are fixed together, here at least by integral pins 611 depending from the top tub 401G and fixedly received in integral sockets 612 upwardly opening in the bottom tub 610.

The inverted top tub 401G (FIG. 2) comprises upstanding, spaced, front and rear valve barrels 402G and 403G respectively. The valve barrels 402G and 403G depend below the sidewall 405G of the top tub 401G. The front barrel 402G extends farther above the top wall 410G than does the rear barrel 403G. The valve barrels 402G and 403G house respective suction and irrigation valve units 651 and 650 hereafter discussed.

An elongate rigid conduit 430G (FIG. 2) is fixed, and preferably integrally molded, at the top of the top tub opposite side wall 404G. To facilitate sealed removable attachment of a surgical tip TP (FIG. 1) engagable (e.g. through a cannula CA) with a surgical site SU, the conduit front end portion 431G may be externally threaded in front of an annular seal ring groove 434G (FIG. 2) which receives a resilient seal ring (e.g. an O-ring 437G). The threads are here shown as broken by oppositely facing flats 616. The conduit rear end portion 432G may be of enlarged diameter and internally threaded to receive a closure plug 440G in sealed, removably fixed relation therein. A resilient seal ring (e.g. an O-ring 442G) on the closure plug 440G provides a liquid seal with the conduit 430G. In the embodiment shown, an annular, internally and externally threaded adapter 620 may be radially interposed between the threaded portions of the conduit rear portion 432G and plug 440G. Removal of the plug 440G and/or adapter 620 allows insertion of a variety of surgical instruments (e.g. an electrocautery probe) forwardly through the central through passage 441G of the conduit 430 to engage the surgical site SU (FIG. 1), for example as discussed in more detail in the above mentioned application incorporated by reference herein.

Irrigation liquid and suction ducts 624, 625 and 626, 627 (FIG. 3A) are fixed to, and preferably integrally molded in, the top wall 410G (FIG. 3A) of the top tub 401G. The irrigation duct 624, 625 has rear and front portions 624 and 625 respectively which flank the front (irrigation) valve barrel 402G. The suction duct 626, 627 has rear and front portions 626 and 627 which flank the rear (suction) valve barrel 402G. The front duct portions 625 and 627 intersect the conduit 430G. The ducts 624, 625 and 626, 627 extend generally rearwardly at an acute angle (here about 220 and preferably between 15 and 30°) to the conduit 430G.

Figure 3A:
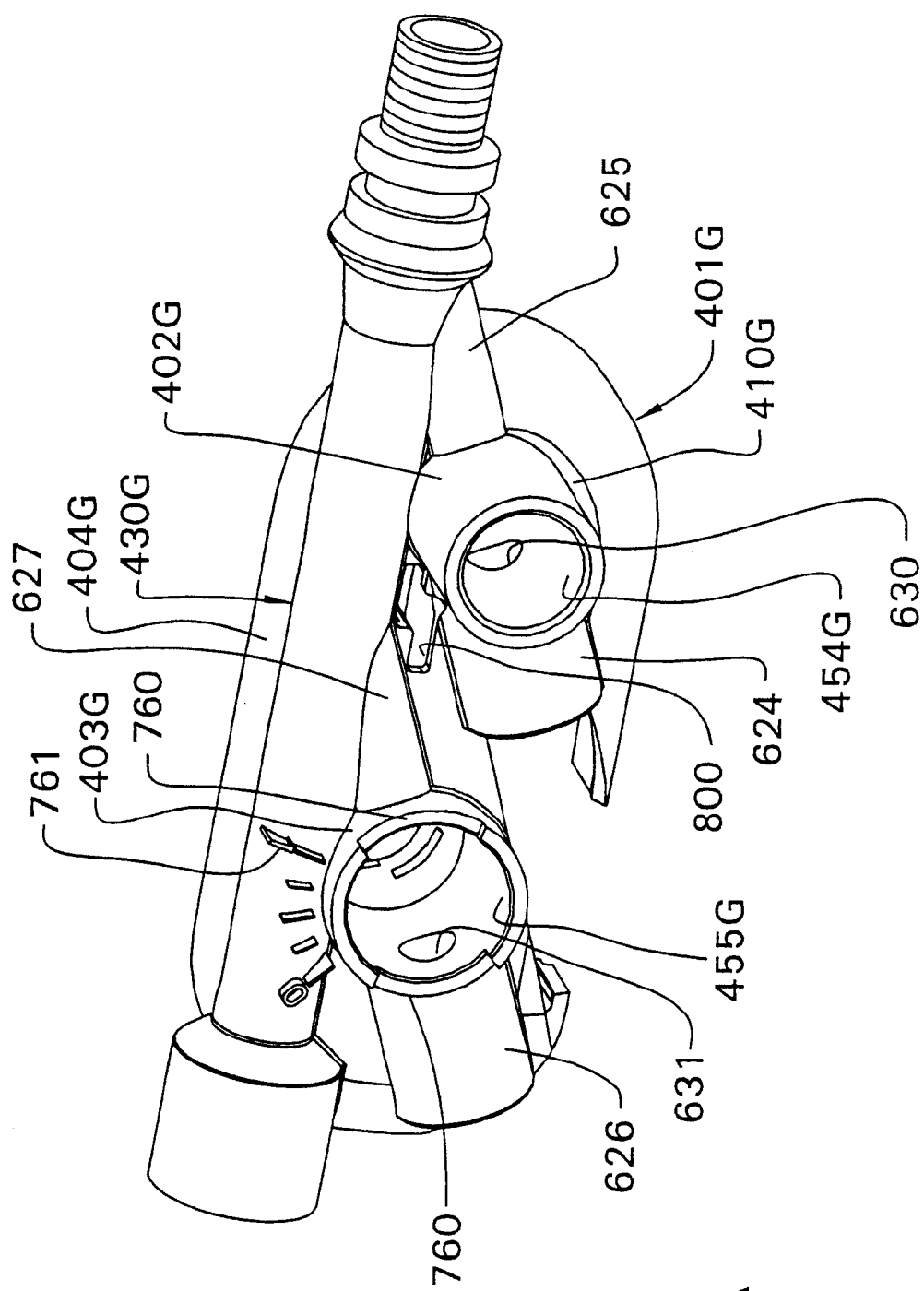
FIG. 3A is a pictorial view of the inverted top tub of the FIG. 1 handpiece.

The ducts 624, 625 and 626, 627 have respective, coaxial, through passages 630 and 631 (FIG. 3B) whose central length axes are parallel to each other and are coplanar with the central length axis of the conduit 430G. The through passages 630 and 631 communicate with the central through passage 441G of the conduit 430G and extend rearwardly and angularly therefrom diametrically through the valve barrels 402G and 403G respectively and open through the rear ends of the ducts 624, 625 and 626, 627 respectively. The central length axes of the irrigation and suction passages 630 and 631 perpendicularly intersect respective upstanding length axes of upstanding, coaxial, bores 454G and 455G, respectively, of the front and rear valve barrels 402G and 403G respectively, as generally seen in FIGS. 3A and 3B.

The rear portions of the through passages 630 and 631 are defined by respective nipples 632 and 633 (FIG. 3B) which are fixed to and extend rearward from the valve barrels 402G and 403G respectively. The nipples 632 and 633 are disposed radially loosely in generally rearwardly opening duct recesses 634 and 635 respectively to enable the nipples 632 and 633 to sealingly and releasably fixedly receive thereon corresponding ends of a flexible irrigation supply tube 23G and flexible suction tube 33G, respectively. In this way, the conduit 430G (FIG. 2) may communicate, e.g. as in the incorporated-by-reference application, through a pump unit 10G with an irrigation liquid source IL and suction source SS through the respective through bores 454G and 455G (FIG. 3B) of the valve barrels 402G and 403G, respectively.

Figure 3B:
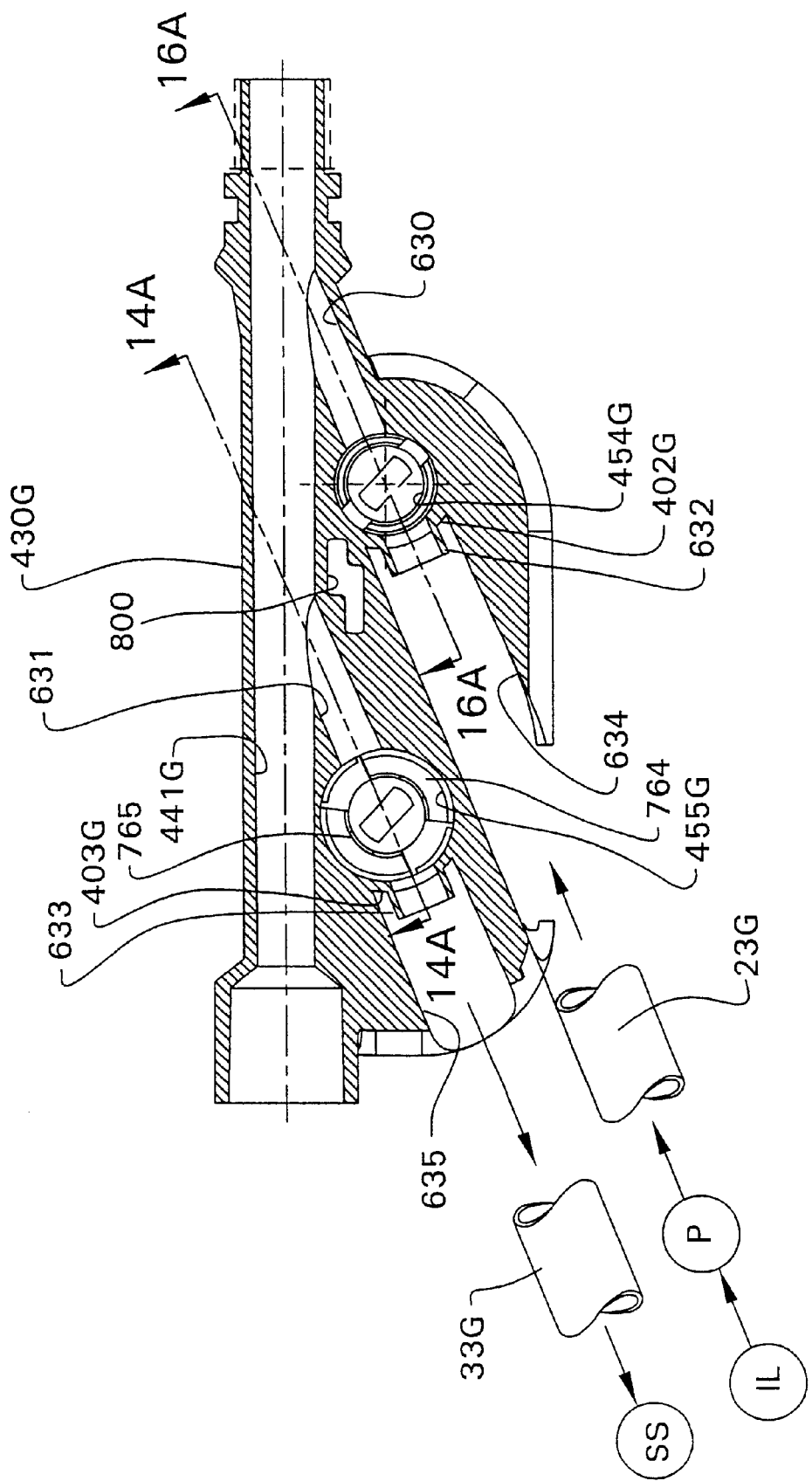
FIG. 3B is a sectional view of the FIG. 1 handpiece taken along the common plane of the length axes of the irrigation and suction through passages and the communicating conduit.

A generally rearward opening hole 640 at the join of the top and bottom tubs 401G and 610, and a generally rearward opening notch 641 (FIG. 1) in the top portion of the inverted top tub 401G, open rearward from the recesses 634 and 635 respectively and are sized to allow easy insertion of the flexible tubes 23G and 33G respectively into such recesses and thus into sealed engagement on the respective nipple 632 and 633 (FIG. 3B). A generally upward and sideward opening notch 642 in the central bottom edge of the top tub 401G, between the recess 63A and hole 640, aids installing the tube 23G on the nipple 632.

The bores 454G and 455G (FIG. 2) of the respective valve barrels 402G and 403G accommodate respective irrigation suction and valve units 650 and 651.

The suction valve unit 651 (FIG. 2) includes a suction leak control sleeve 660, a coil spring 661, a seal spool 662, a valve body 663, an annular seal (e.g. an O-ring) 664 and a push button 665.

Figure 4B:
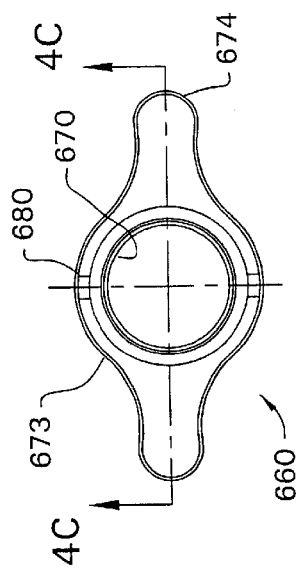
FIG. 4B is a bottom view of the FIG. 4A sleeve.
Figure 4D:
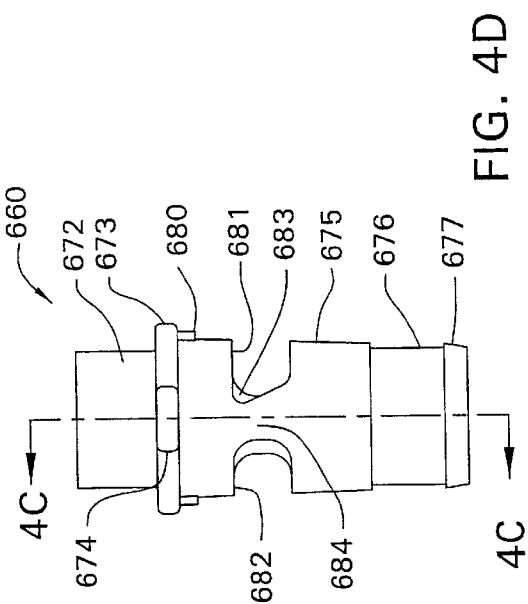
FIG. 4D is a side view of the FIG. 4A sleeve.
Figure 4A:
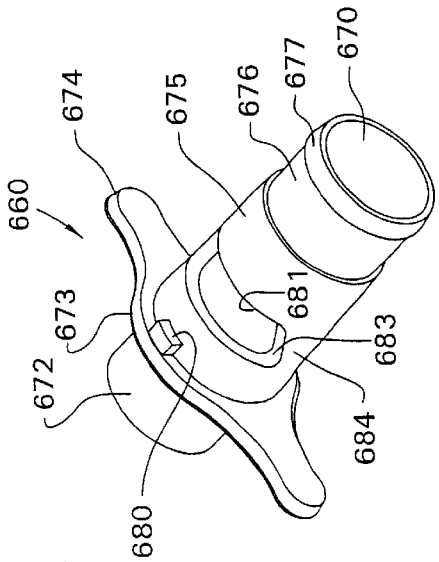
FIG. 4A is a pictorial view of the suction leak control sleeve of the FIG. 1 handpiece.
Figure 4C:
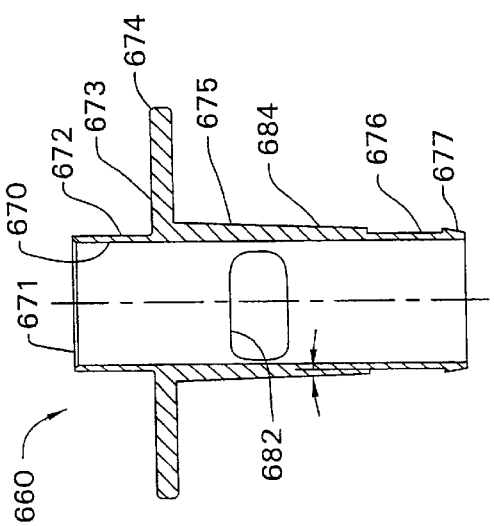
FIG. 4C is a central cross sectional view of the FIG. 4A sleeve substantially taken on the line 4C—4C of FIG. 4D.

The sleeve 660 (FIGS. 4A–D) is a generally tubular member having a substantially cylindrical through bore 670 extending longitudinally therethrough and topped by a radially inwardly sloped chamfered edge 671 (FIG. 4C). From the top, the outer periphery of the sleeve 660 includes a generally cylindrical top portion 672, a radially outwardly extending flange 673 having circumferentially spaced (here diametrically opposed), finger engagable, rotation inducing arms 674, an intermediate portion 675, a shallow, axially elongate, cylindrical groove 676 and a downward tapered bottom rim 677. The intermediate portion 675 is genty (hereat an angle of 1° to 3°, preferably 2°) downwardly tapered. Substantially rectangular keys 680 are fixed at the joinder of the flange 673 to the tapered intermediate portion 675. The keys are preferably diametrically opposed and circumferentially offset by about 90° from the arms 674. Circumferentially elongate windows 681 and 682 open through the peripheral wall of the sleeve 660 intermediate the height of the intermediate tapered portion 675, in axially spaced relation between the keys 680 and groove 676. The top and bottom edges of the windows 681 and 682 are substantially parallel and lie in corresponding, substantially diametrical planes. The ends of the windows are somewhat rounded, as seen in FIGS. 4A, C and D. Indeed, one end of the windows 681 is, along its upper edge provided with a tapered circumferentially extending indent 683 (FIGS. 4A and 4D). The windows are circumferentially spaced by peripheral wall portions 684 of the sleeve intermediate portion 675.

The valve body 663 (FIGS. 5A–E), from the top, includes an elongate, generally cylindrical trunk 690, an elongate, reduced diameter, constant cross-section waist 691, a radially outwardly extending hip flange 692 having the same outside diameter as the trunk 690, and a pair of depending, downwardly divergent, resiliently bendable, leaf-spring-like legs 694 terminating at their lower ends in respective, radially outwardly extending, somewhat upward angled feet 695.

Figure 2:
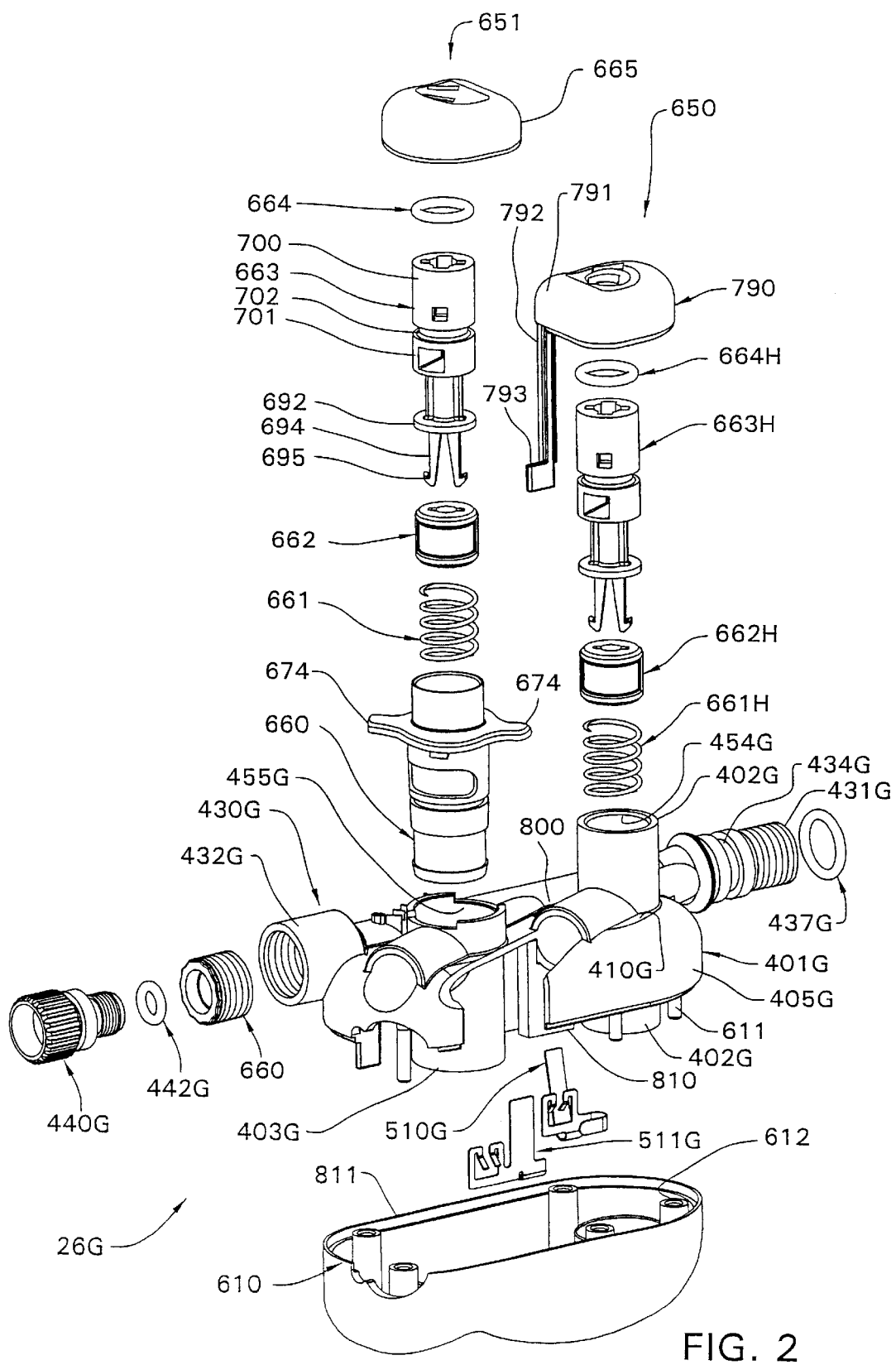
FIG. 2 is an exploded view of the FIG. 1 handpiece.

The trunk 690 is separated into top and bottom portions 700 and 701 by an annular groove 702 which receives the seal ring 664 (FIG. 2). A cross-shaped (cruciform) recess 703 opens coaxially through the top face 704 of the trunk 690. A generally rectangular cross-section, diametrical through opening 705 extends through the trunk top portion 700 in spaced relation above the groove 702. The diametrical through opening 705 is at the bottom of and in communication with the cruciform recess 703. Two diametrically opposed axial grooves 710 of the cruciform recess 703 intersect the diametrical through opening 703. The central bottom surface of the cruciform recess 703 is defined by a coaxial, symmetrical cross-section, upstanding wedge 711 (FIG. 5D) having upwardly convergent sides, each facing a corresponding cruciform recess axial groove 710 and end of the diametrical through opening 705. The wedge 711 thus projects upward into the diametrical through opening 705. The lateral width of the wedge 711 is substantially less than the distance between the opposed bight faces of the axial groove 710, such that the wedge 711 is substantially spaced from the top of the diametrical through opening 705 and the opposed faces of the annular grooves 710, and allows considerable space at the intersection of each such axial groove 710 with the corresponding end of the diametrical through opening 705, as readily seen in FIG. 5D.

Figure 5A:
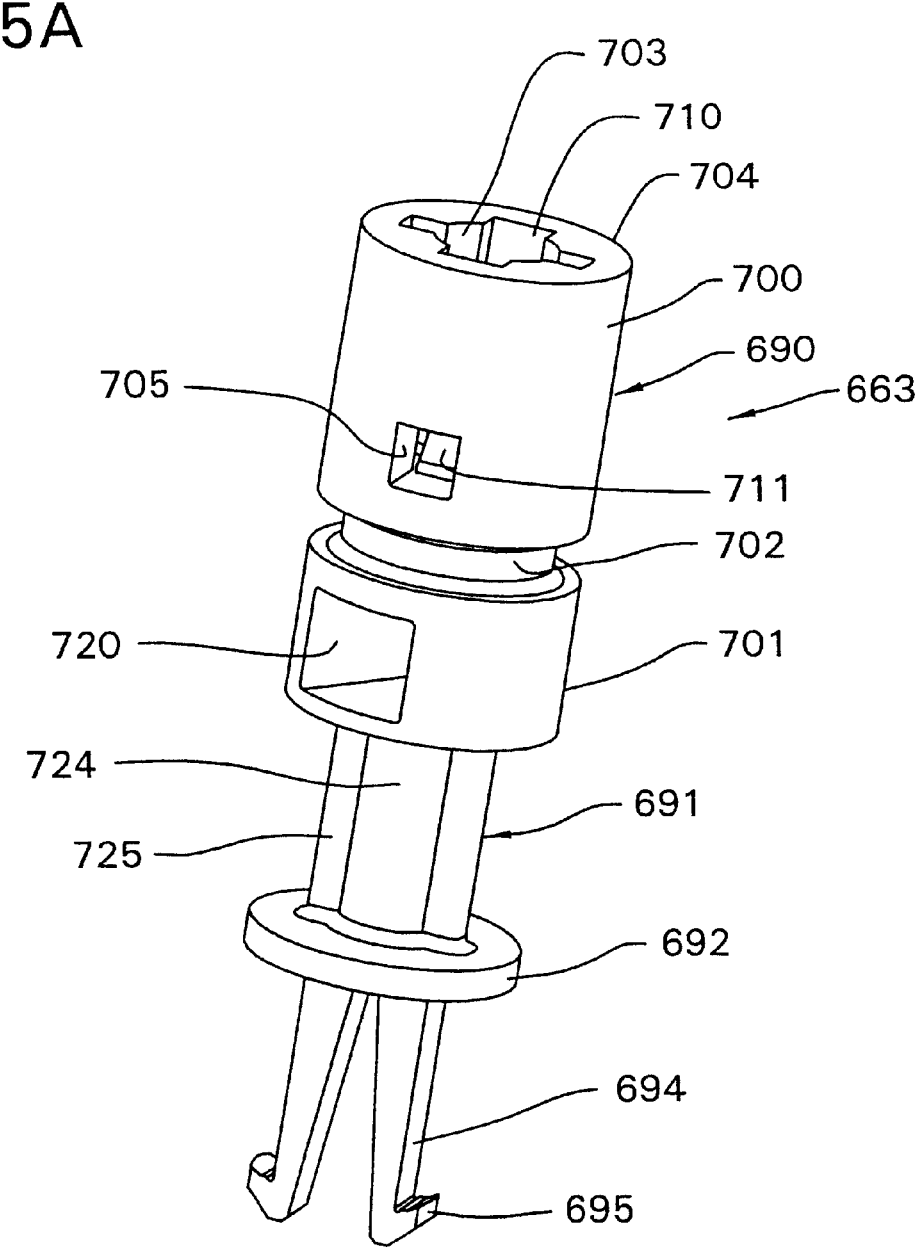
FIG. 5A is a pictorial view of the suction valve body of the FIG. 1 handpiece.
Figure 5C:
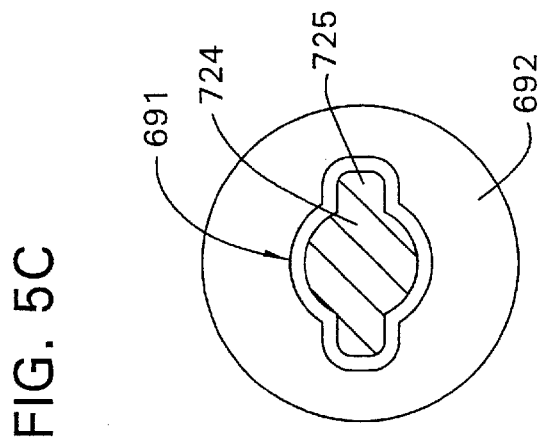
FIG. 5C is an enlarged cross sectional view taken on the line 5C—5C of FIG. 5B.
Figure 5B:
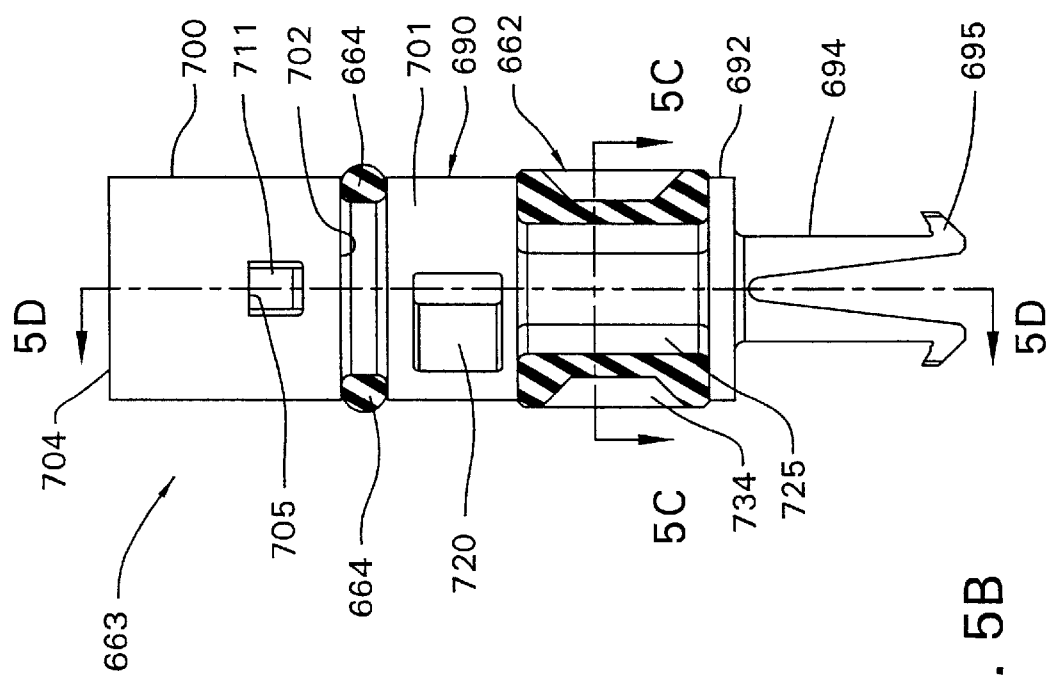
FIG. 5B is a partially broken elevational view of the FIG. 5A valve body.
Figure 5E:
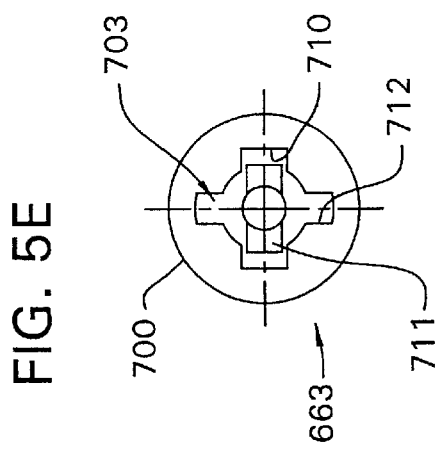
FIG. 5E is a top view of the FIG. 5A valve body.
Figure 5F:
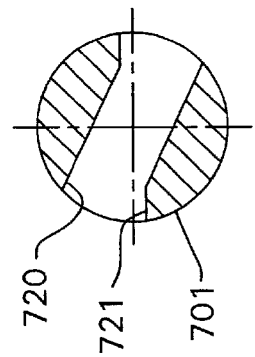
FIG. 5F is a sectional view taken substantially on the line 5F—5F of FIG. 5D.

A diametrical through passage 720 (FIGS. 5A and 5B) in the trunk bottom portion 701 is here of substantially rectangular cross-section, which cross-section is substantially larger than that of the diametrical through opening 705 and occupies much of the height of the trunk bottom portion 701. In the embodiment shown, the diametrical axes of the through opening 705 and through passage 720 are slightly circumferentially offset, as well as being axially spaced apart. The outer ends of the diametrical through passage 720 are each circumferentially widened by a clockwise facing (seen from the top) bevel 721 (FIG. 5F).

The waist 691 (FIG. 5A) comprises a reduced diameter, longitudinally extending, cylindrical core 724 flanked by diametrically outwardly protruding, axially extending ribs 725.

Figure 6B:
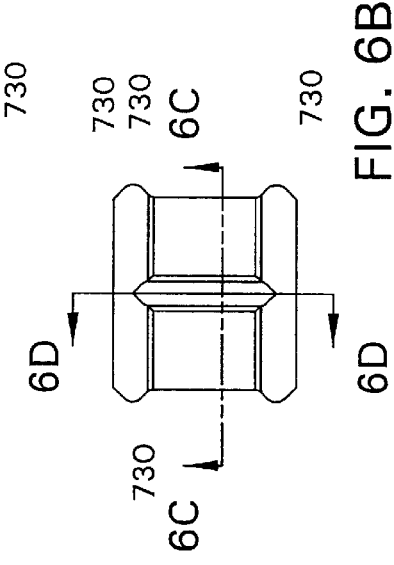
FIG. 6B is an elevational view of the FIG. 6A seal spool.
Figure 6D:
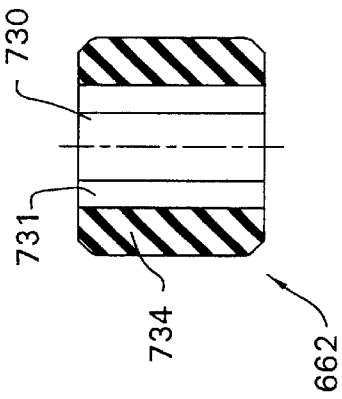
FIG. 6D is a sectional view substantially taken on he line 6D—6D of FIG. 6B.
Figure 6A:
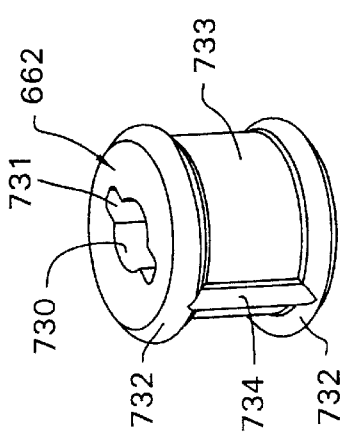
FIG. 6A is a pictorial view of the seal spool of the FIG. 1 handpiece.
Figure 6C:
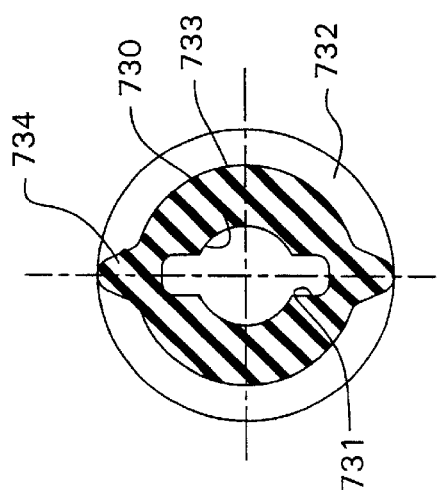
FIG. 6C is a sectional view substantially taken on the line 6C—6C of FIG. 6B.

The seal spool 662 (FIGS. 6A–6D) has a coaxial through passage 730 whose inner periphery is indented by two axially extending, diametrically opposed grooves 731. The spool has a coaxial radially outwardly extending circular end flanges 732 of generally rounded periphery and which are axially symmetrically opposed as seen in FIG. 6B. The end flanges 732 axially flank a substantially cylindrical midportion 733 of reduced diameter. Ribs 734 protrude radially outward from the central portion 733 and extend axially between the flanges 732. The ribs 734 are diametrically oppositely extending and preferably are coplanar with the grooves 731 and with the central length axis of the seal spool 662. The seal spool is of resiliently deformable material, preferably as conventionally used for fluid seals, such as a suitable resilient polymer or natural rubber.

Figure 7C:
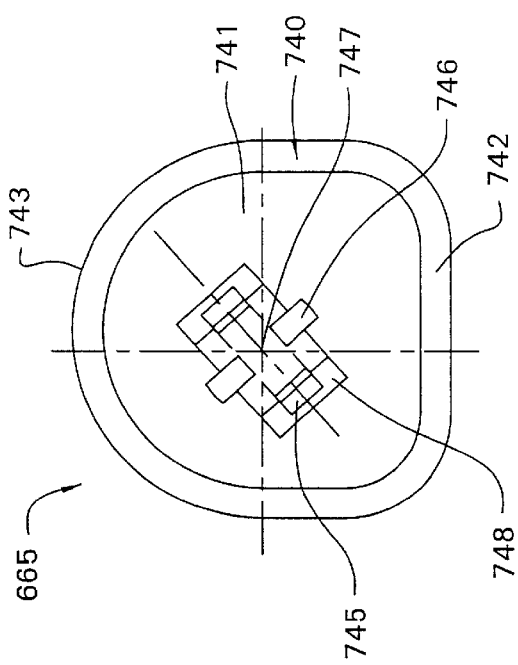
FIG. 7C is a bottom view of the FIG. 7A pushbutton.
Figure 7A:
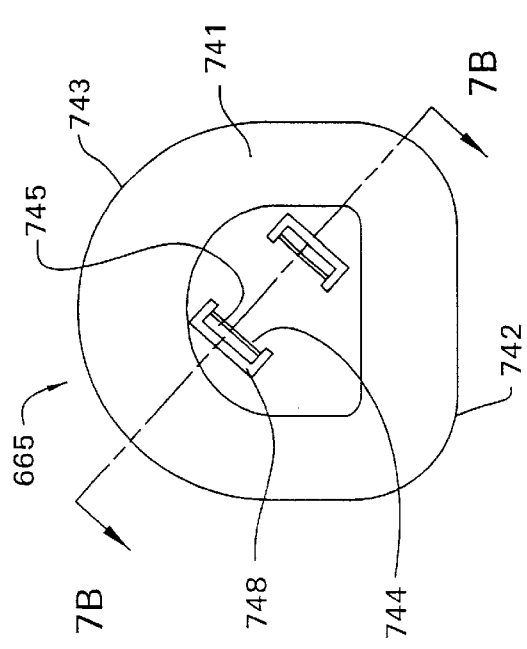
FIG. 7A is a top view of the suction pushbutton of he FIG. 1 handpiece.

The pushbutton 665 (FIGS. 7A–7C) comprises an inverted shallow cup 739 of generally D-shape in plan (FIG. 7A), having a peripheral wall 740 and an end wall 741. A portion 742 of the peripheral wall 740 is substantially straight and the diametrically opposite portion 743 of the peripheral wall 740 is convexly rounded. At a location preferably slightly offset rightwardly and above center (as seen in FIG. 7A), a pair of laterally spaced, leaf-spring-like legs 744 (FIG. 7B) project slightly divergently from the interior face of the push-button end wall 741 toward the open end of the cup 739, and terminate in acutely upwardly angled, oppositely projecting feet 745, which here extend just beyond the free edge of the push-button peripheral wall 740. Laterally opposed and spaced posts 746 similarly extend from the interior surface of the push-button end wall 741 toward the open end the cup 739 and beyond the free edge of the peripheral wall 740 to about same extent as the feet 745. The legs 744 and posts 746 alternate circumferentially around a common center, indicated at 747 in FIG. 7C, and are preferably equally circumferentially spaced. Spaced opposed holes 748 open through the push-button end wall 741 (FIGS. 7A and 7B) along the outboard edges of the corresponding legs 744.

The suction valve unit 651 may be assembled as follows. The O-ring 664 (FIG. 2) is resiliently stretched over and slid down along the top portion 700 of the valve body 663 and snaps into the annular groove 702. The resilient seal spool 662 is radially resiliently stretched sufficient to pass upward over the legs 694 and hip flange 692 and snap into place between the trunk bottom portion 701 and flange 692, with waist ribs 725 (FIG. 5C) received snugly in circumferentially fixing relation in the axial grooves 731 in the seal spool 662. This fixes the seal spool 662 on the valve body 663 generally indicated in FIG. 5B.

Figure 5D:
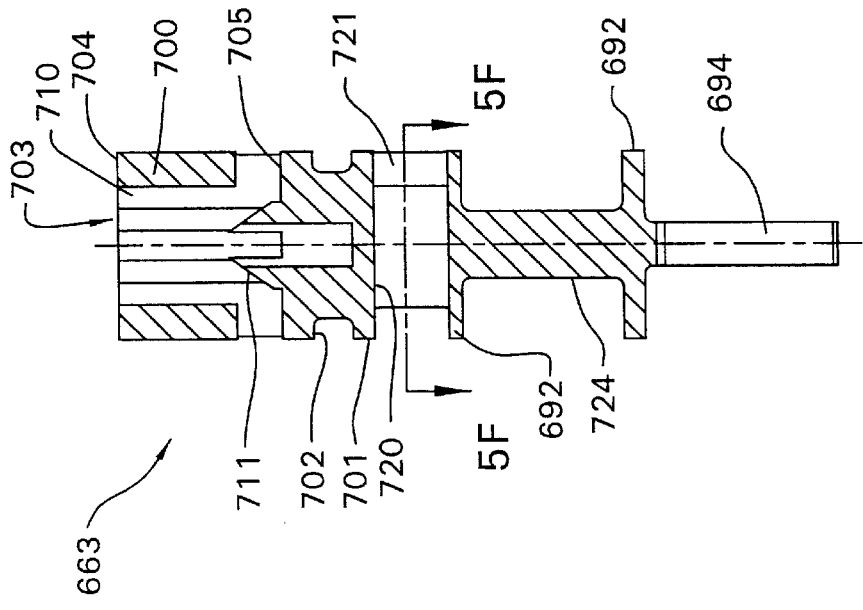
FIG. 5D is a central cross sectional view substantially taken on the line 5D—5D of FIG. 5B.
Figure 7B:
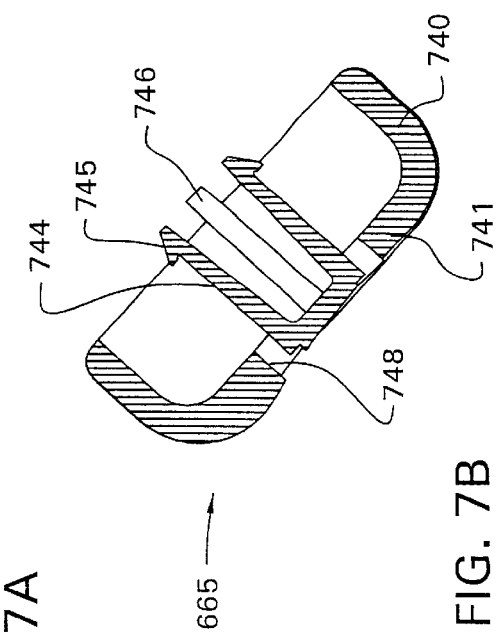
FIG. 7B is a sectional view substantially taken on the line 7B—7B of FIG. 7A.
Figure 8A:
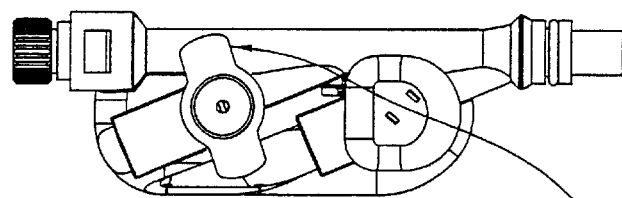
FIG. 8A is a fragmentary schematic top view of the FIG. 1 handpiece in the suction leak closed, suction valve closed condition.
Figure 8B:
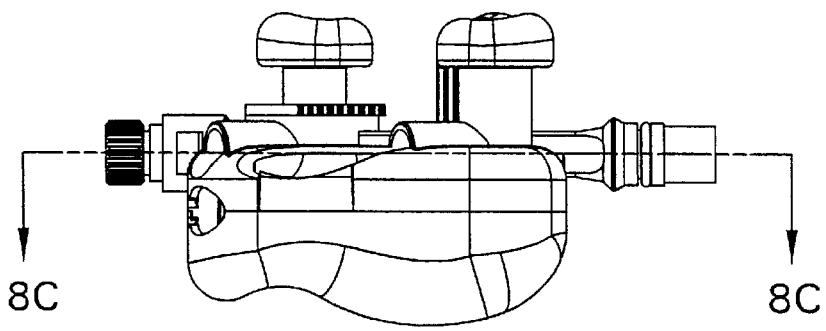
FIG. 8B is a fragmentary schematic side view of the FIG. 8A handpiece.
Figure 14A:
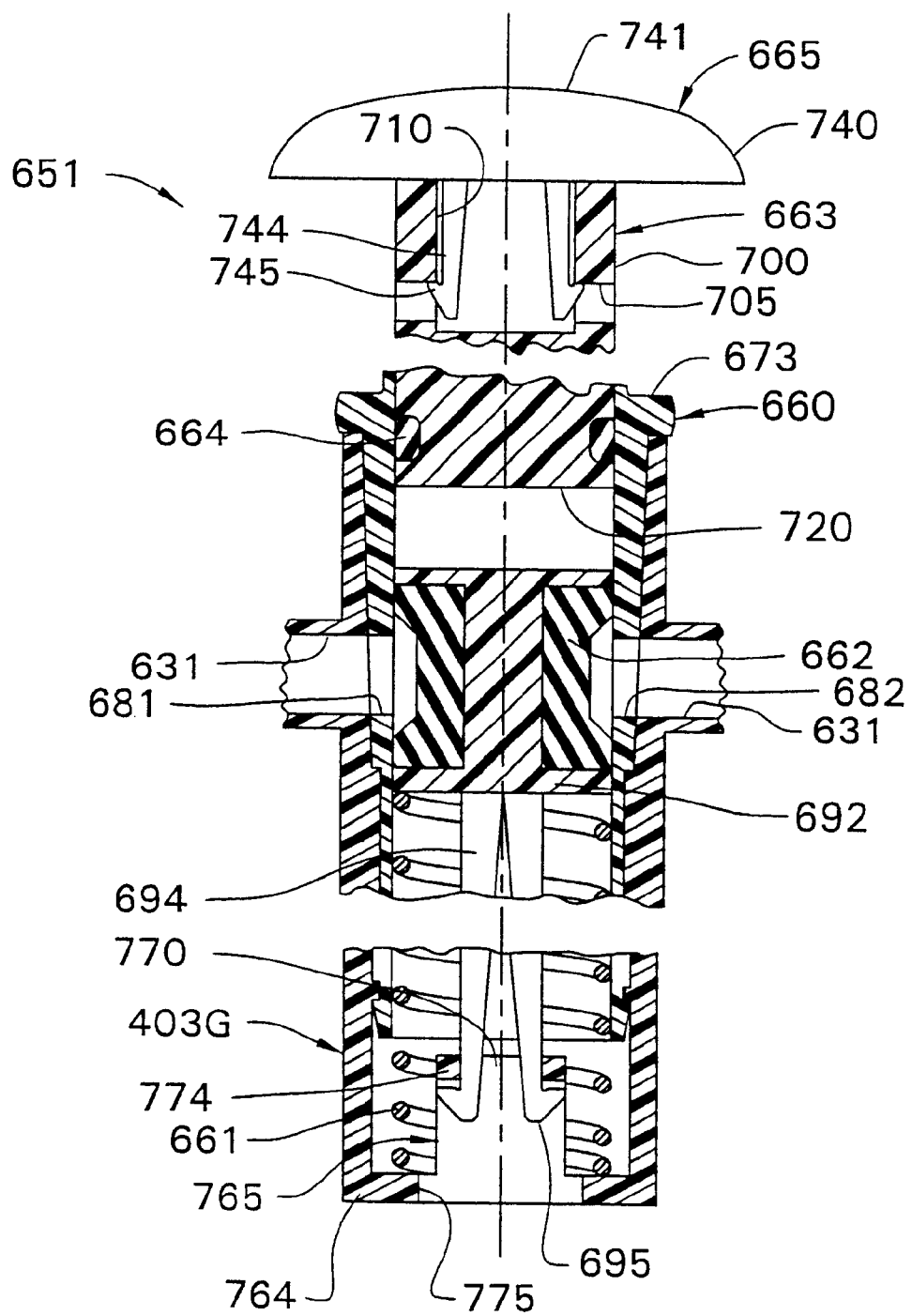
FIG. 14A is an enlarged, fragmentary, schematic central cross-sectional view substantially taken on the line 14A—14A of FIG. 3B and showing the suction valve in its closed condition.

Thereafter, the push-button 665 (FIG. 7B) is snap fitted atop the valve body 663 as generally indicated in FIGS. 1 and 14A. More particularly, the push-button legs 744, with their feet 745, are pressed downward into the valve body axial grooves 710 (FIGS. 5D and 7B). Simultaneously, the push-button posts 746 enter the remaining axial grooves 712 of the cruciform recess 703 and the top of the valve body 663. The springy legs 744 press their feet 745 radially outward against the outer walls of the grooves 710. Continued insertion of the feet 745 into the valve body diametrical through opening 705 allows the springy legs 744 to spring apart and seat their feet 745 outward of their respective valve body axial grooves 710 to entrap same under the top, outboard faces of the diametrical through opening 705, whereafter the push-button end wall 741 comes to rest on the top 704 of the valve body 663, with the peripheral wall 740 of the push-button 665 overhanging part of the valve body top portion 700.

While not normally done, it is possible to remove the push-button 665 from the valve body 663 by inserting a slim rigid probe (not shown) radially into the outer end of the diametrical through opening 705 to press the corresponding foot 745 radially inward against the wedge 711 which displaces it upward along the corresponding groove 710. This can be done to both feet 745 but doing it to one is normally sufficient to pop the push-button 665 off the valve body 663.

Similarly, a slim rigid probe inserted in one or both of the holes 748 (FIG. 7B) can resiliently bend the corresponding leg 744 of the push-button 665 radially inward to release the foot 745 from the diametrical through opening 705, to thereby pop the push-button 665 off the top of the valve body 663 (FIG. 5D).

Figure 3D:
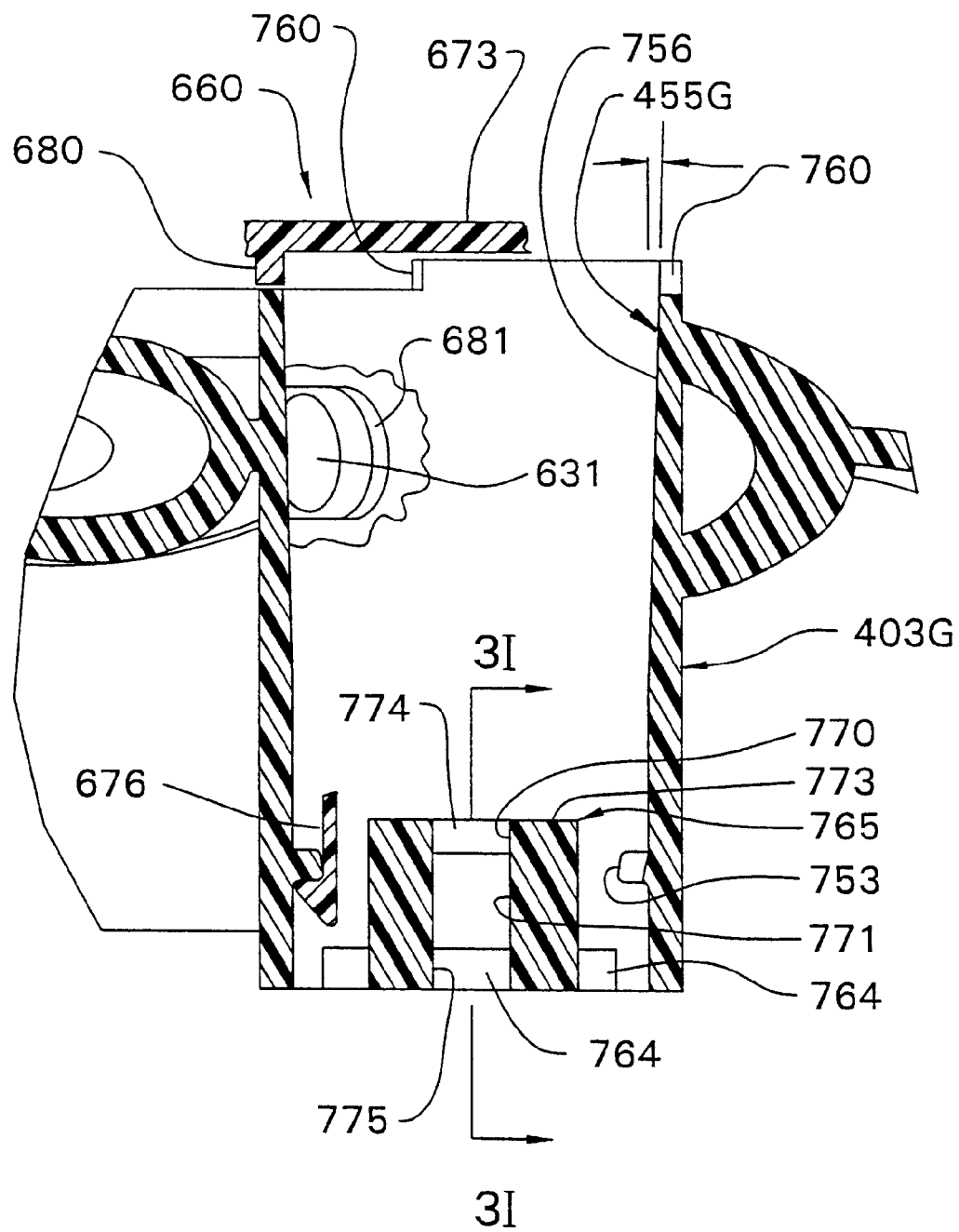
FIG. 3D is a fragmentary, partly broken, sectional view generally taken on the line 3D—3D of FIG. 3C.
Figure 3E:
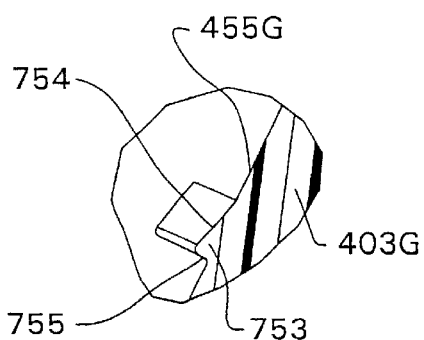
FIG. 3E is an enlarged fragment of FIG. 3D, detailing one of the sleeve retaining ridges.
Figure 3G:
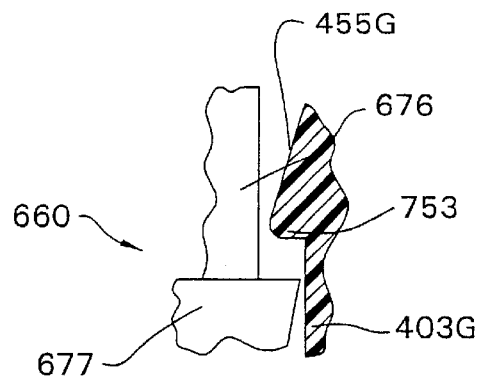
FIG. 3G shows a fragment of FIG. 3E and illustrates the retained engagement of the shell by the FIG. 3E ridge.

The sleeve 660 (FIG. 2) is of a generally self-lubricating, somewhat resilient and seal-like material, such as polyethylene. The sleeve 660 inserts down into the open upper end of the suction valve bore 455G. The sleeve tapered bottom rim 677 (FIG. 4A) resiliently snaps down over, and is retained against upward displacement by, circumferentially spaced, semi-circular ridges 753 (FIG. 3E) fixed near the bottom of the valve bore 455G. The ridges 753 have sloped, upwardly and radially inward facing ramp surfaces 754 and downward facing surfaces 755 (FIG. 3E). The slope of the ramp surface 754 preferably compliments the radially outward and downward facing slope of the sleeve tapered bottom rim 677. The semi-circumferential ridges 753 thus fixedly retain the sleeve 660 in its installed position within the valve bore 455G.

The upper portion 736 of the suction valve bore 455G is downwardly convergently tapered at angle in complement to and preferably the same as that of the sleeve tapered intermediate portion 675 (FIG. 4C), to provide a taper-snugged, rotative seal therebetween in the assembled handpiece 26G.

The upper edge of the suction valve barrel 403G (FIGS. 3A and 3D) is stepped to form a pair of axially shallow, diametrically opposed notches 760. As seen from the top, the centers of the notches 760 are on an imaginary line angled slightly clockwise from the common central plane of the valve bore 455G and suction duct 626. With the sleeve installed in the suction valve bore 455G, and as shown schematically in FIG. 3D, the sleeve flange 673 rides atop the valve barrel 403G and the sleeve keys 680 ride in respective ones of the notches 760 to limit rotation of the sleeve 660 to an acute angle arc of about 50° to 70°, preferably of about 60°. Radiating line indicia 761 (FIGS. 3A, 8C and 9C) are fixed (e.g. molded onto) the top of the conduit 430G, are on radii of the central axis of the suction valve bore 455G, and are spaced along an arc over which one of the sleeve arms 674 rotates to show the user the rotative position of the arms 674, and thereby of the windows 681 and 682 of the sleeve 660 with respect to the suction through passage 630. The windows 681 and 682 are located circumferentially on the sleeve such that they continuously open to the suction through passage 631 through the rotation of the sleeve 660, defined by interference of the keys 680 and notches 760 and shown by the rotation of the corresponding sleeve arm 674 along the arc of the indicia 761.

Figure 3H:
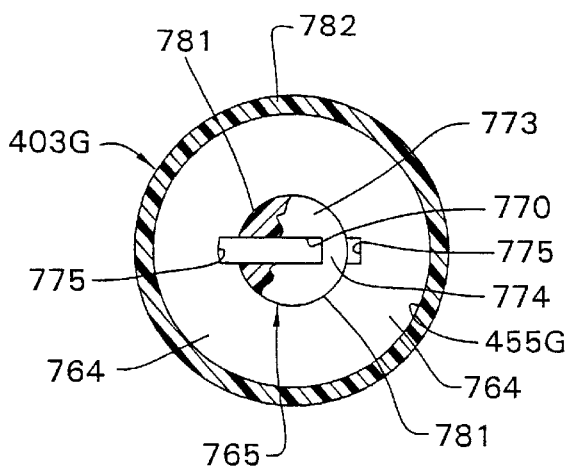
FIG. 3H is an enlarged fragment of FIG. 3B showing the interior bottom portion of the suction valve barrel 403G.
Figure 3I:
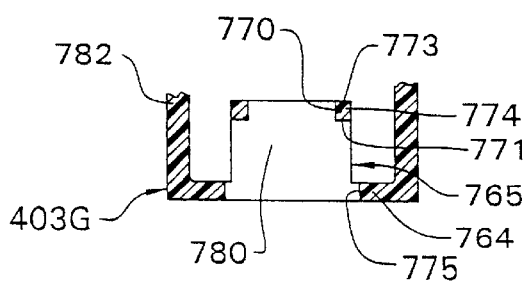
FIG. 3I is a fragmentary sectional view substantially taken on the line 3I—3I of FIG. 3D.
Figure 3F:
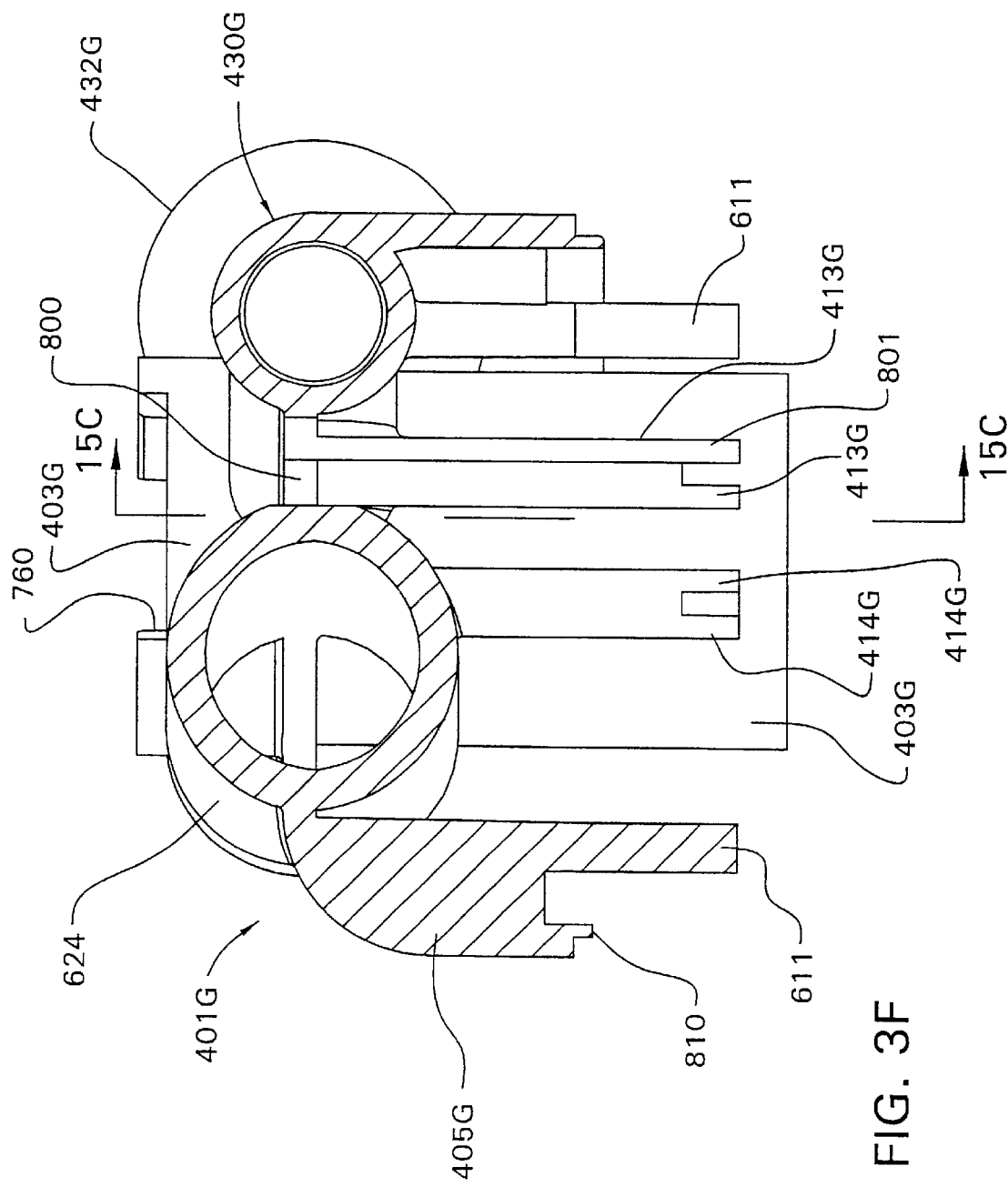
FIG. 3F is an enlarged sectional view substantially taken on the line 3F—3F of FIG. 3C.
Figure 3J:
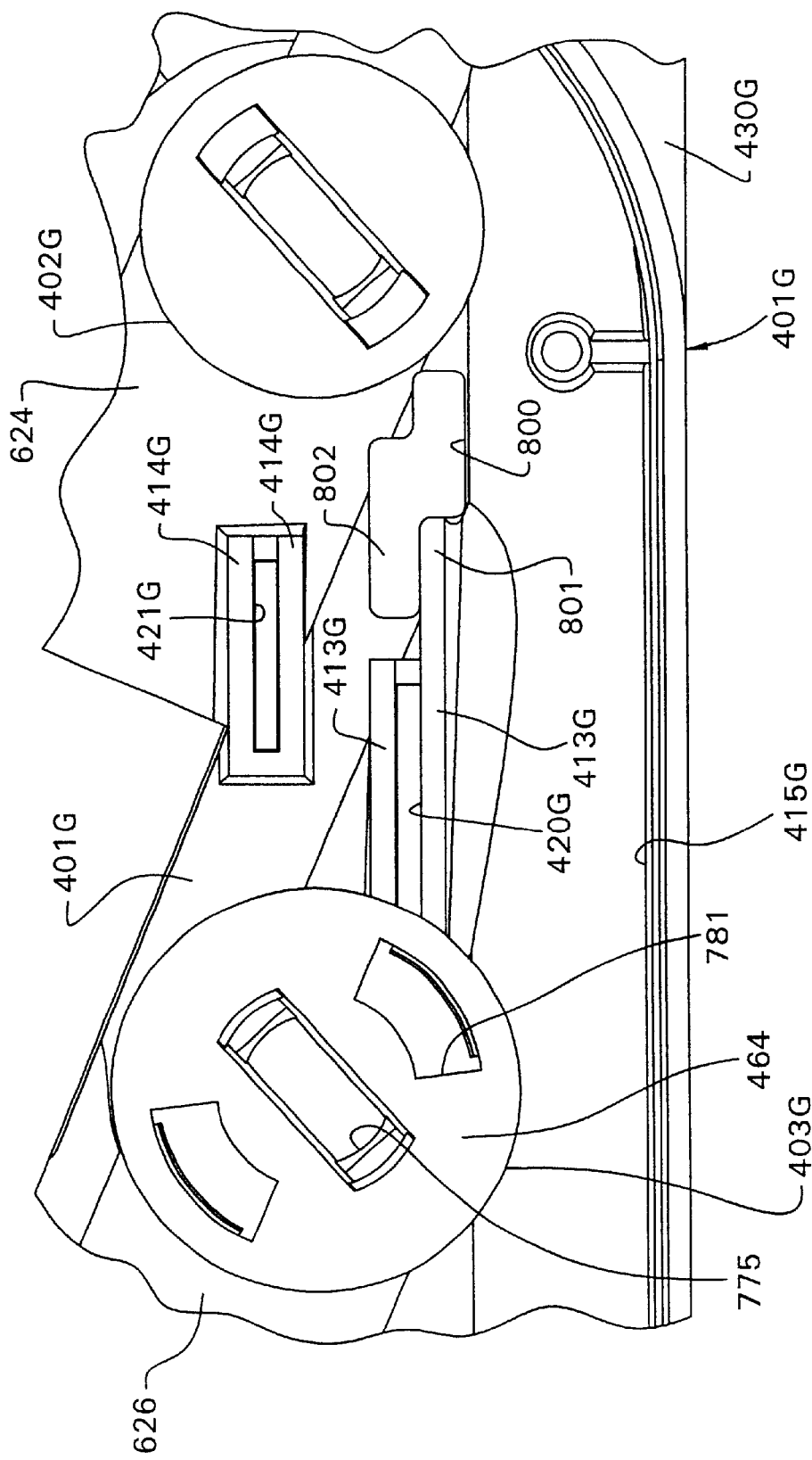
FIG. 3J is an enlarged fragment of FIG. 3C.

Fixed to, and coaxially upstanding from, the bottom wall 764 of the suction valve barrel 403G (FIGS. 3H, 3I and 14A) is a circular, cylindrical (or slightly upward tapered) boss 765. An upstanding, generally rectangular, cross-section hole 771 extends diametrically through the boss 765 from the barrel bottom wall 764 (FIG. 3D) partway to the top of the boss. A generally rectangular, diametrical top slot 770 extends partway across the top 773 of the boss, opens to the mid-portion of the diametrical hole 771 and forms an upward continuation of the latter. The diametrical top hole 771 and slot 770 leave chordal peripheral rim portions 774 diametrically opposed at the top portion of the boss 765. A generally rectangular, diametrical bottom slot 775 opens through the bottom wall 764 and forms a smooth downward continuation of the diametrical top hole 771. The bottom slot 770, top hole 771 and bottom slot 775 are of the same width and have a common central plane, as well as common side walls 780, as in FIG. 3I.

Arcuate openings 781 (FIG. 3H) through the barrel bottom wall 764 are diametrically opposed and extend from the boss 765 to the peripheral wall 782 of the suction valve barrel 403G.

With the sleeve 660 already installed in the suction valve barrel 403G as above described, the assembling of the suction valve unit 651 (FIG. 2) may continue as follows. The spring 661 is dropped into the sleeve 660, wherein the spring 661 (FIG. 14A) rests on the bottom wall 764 of the valve barrel 403G with its bottom portion surrounding the boss 765.

Thereafter, the valve body 663, with the seal spool 662, annular seal 664 and push button 665 installed thereon, as above described, is pushed downward, feet 695 first, into the sleeve 660 such that the legs 694 and feet 695 loosely enter the interior of the spring 661 and the hip flange 692 comes to rest atop the spring 661. Further insertion of the valve body 663 causes the descending hip flange 692 to partially compress the spring 661 as the feet 695 enter, are resiliently pushed toward each other by, and pass downward through the generally rectangular slot 770 (FIGS. 3H, 3I and 14A) in the top of the table 765 whereupon the feet spring 695 resiliently spring apart so as to abut and become entrapped beneath the chordal peripheral rim portions 774 of the table 765. The spring 661 resiliently urges the feet 695 upward against such chordal peripheral rim portions 774.

This leaves the suction valve unit 651 in its normal, at rest, closed, axially up position of FIG. 14A, wherein the push button 665 is spaced well above the top of the sleeve 660. In this closed position, the seal spool 662 is vertically centered on the suction leak control sleeve windows 681 and 682 and on the irrigation through passage 631, which are vertically aligned with each other as above discussed with respect to FIG. 3D. Also, in this suction valve unit closed position, the flange 692 is spaced below the windows 681 and 682 and suction through passage 631, whereas in sequence upward therefrom are the suction valve diametral through passage 720, the annular seal 664 and the suction leak control sleeve top flange 673. In this closed position, the resilient top and bottom end flanges 732 of the seal spool 662 snugly engage and circumferentially seal against the interior wall of the sleeve 660, immediately above and below the sleeve windows 681 and 682, and so positively prevent leakage of fluids from the passage. 631 along the interior of the sleeve 660 past the top and bottom sealing spool end flanges 732.

Should for any unexpected reason it be desired to do so, the valve body 663 (FIG. 14A) can be removed from the valve barrel 764 by displacing the feet 695 toward each other sufficient to clear the chordal peripheral rim portions 774 of the boss 765, as by means of a suitable thin probe element (or tweezer like pair of probe elements) inserted upward through the slot 775 in the bottom wall of the valve barrel 403G.

Figure 14B:
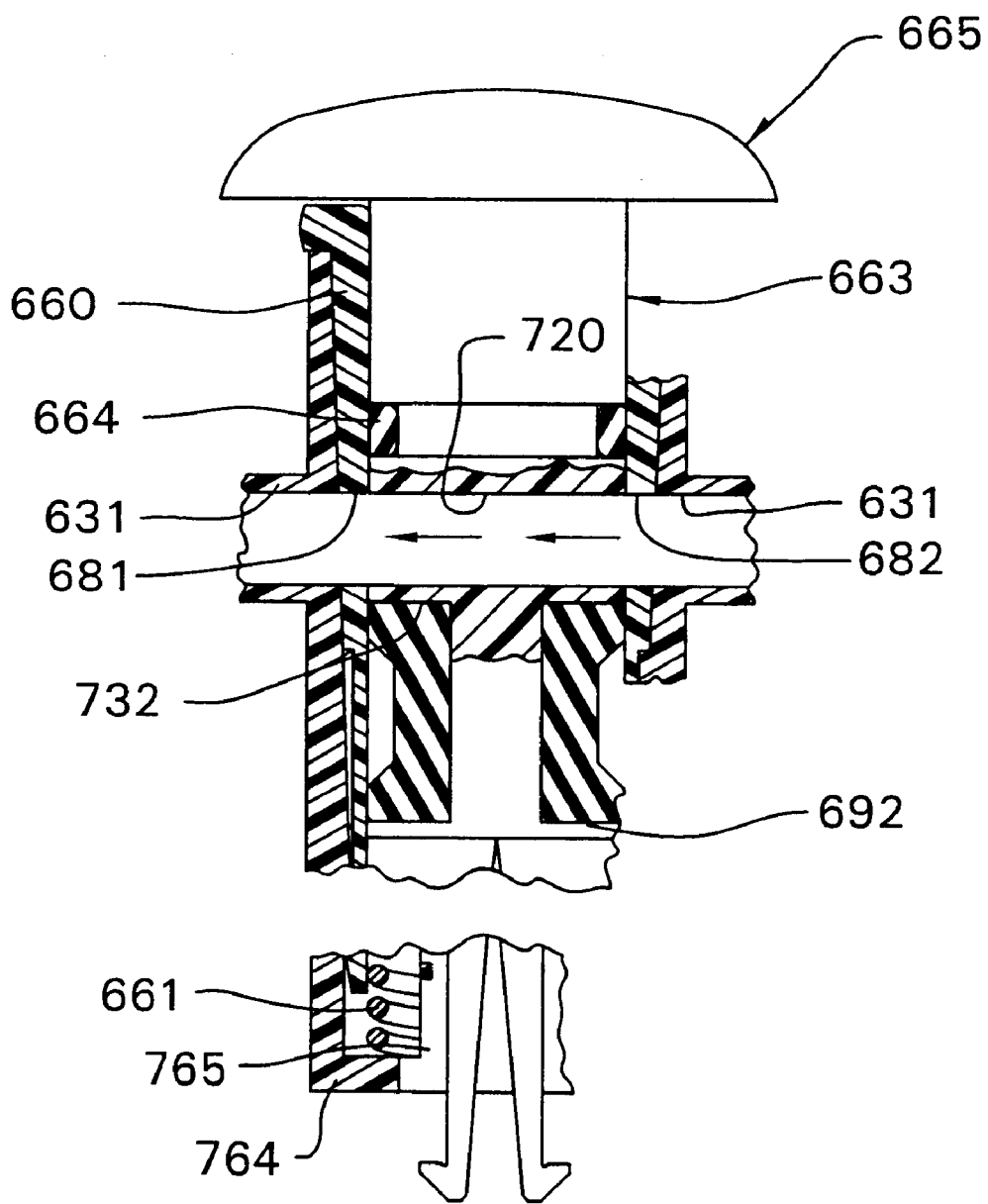
FIG. 14B is a fragment of FIG. 14A but showing the suction valve in its full open condition.

Full manual depression of the push button 665 (FIG. 14B and, for convenience in the illustration, FIG. 1) displaces the valve body 663 downwardly further into the sleeve 660, thus displacing the feet 695 downward below the bottom wall 764 of the valve barrel 403G and abutting the hip flange 692 with the top of the boss. This substantially fully and coaxially communicates the valve body diametral through passage 720 with the sleeve windows 681 and 682 and the suction through passage 631. The suction valve unit 651 is thus now in its normal, full open position.

This provides suction flow from the surgical site SU (FIG. 1), through the front portion of the conduit 430G, the front portion of the through passage 631 (FIG. 14B), the window 681, the valve body diametral through passage 720, the window 682, the rear portion of the suction through passage 631, the nipple 633 (FIG. 3B), the flexible tubing 33G (FIG. 1), to a suction source SS, e.g. conventional hospital operating room suction source. The resilient O-ring 664 and upper end flange 732 of the seal spool 662 circumferentially seal against the inner periphery of the sleeve 660, and thus prevent fluid leakage between the upper and lower portions of the sleeve 660 and the valve body diametral through passage 720.

Upon release of user finger pressure on the push button 665, the spring 661 returns the valve body 663 and push button 665 to their upper, off position of FIG. 14A, thereby closing suction flow through the diametral through passage 720 of the suction valve unit 651.

The suction valve unit 651 is typically opened (by depression of the push button) to remove bits of tissue, entrained in liquid, from the surgical site SU, generally as in the incorporated-by-reference application, although, as seen herein, the suction valve unit 651 differs substantially in structure from that of the incorporated-by-reference application.

Different partial depressions of the suction pushbutton 665 correspondingly partially open the suction valve unit 651 and thus provide different partial (not full) suction flows. However, the user may find it difficult over time to maintain a given partial pushbutton depression location and thus a desired partial suction flow level.

At times it may be desirable to apply a smaller (i.e. partial), constant, adjustable, amount of suction to the surgical site, without the difficulty of trying to accurately set suction flow level by partial depression of the push button or trying to maintain a partially depressed portion of the pushbutton 665 over a period of time. An example would be during removal of smoke from the surgical site SU during electrocautery. One of the types of surgical instruments that may be inserted into the surgical site SU, through the conduit 430G, is a conventional electrocautery probe (not shown).

Thus, the present invention allows the user, without depressing the push button 665, to set a desired partial suction flow from zero to a preselected fraction of the maximum suction flow which would occur if the push button 665 were fully depressed. Moreover, the present invention automatically maintains that set partial suction flow without further attention from the user, until the user elects to change that set partial suction flow (e.g. return it to zero). This partial suction flow provided by the present invention may be referred to as the suction leak, or bypass, flow.

As seen above, with the push button 665 and the valve body 663 in their up position (FIG. 14A), due to the bias of the spring 661 and a absence of manual depression of the push button 665 by the user, suction flow through the valve body 663 is positively prevented because the diametral through passage 720 is raised above and sealed from the suction through passage 631 of the upper inverted tub 401G (FIG. 2). The seal spool 662, in the closed (up) position (FIGS. 8C and 14A) of the suction valve body 663, is interposed in the suction through passage 631. With the suction leak control S sleeve 660 in its FIG. 8C closed rotative position, namely with its arm 674 at the counterclockwise (as seen from the top) end of its arc of rotation, the axially extending seal spool ribs 734 seal against the portions 684 of the peripheral wall of the suction leak control sleeve 660, which portions 684 circumferentially separate the windows 681 and 682. Thus, the seal spool ribs 734 positively block suction flow therepast. Thus, there is no suction flow through the handpiece 26G (FIG. 2) at all, because the valve body diametral through passage and the suction leak path (hereafter discussed) past the seal spool 662 are both blocked.

However, to set a desired partial suction flow in the suction through passage 631, (e.g. for electrocautery smoke evacuation), the user simply rotates the arms 674 in a clockwise (as seen from the top in FIG. 9C) direction, until the desired level of partial suction is achieved. The material of the sleeve 660 is somewhat self-lubricating, such that a modest rotative force on the sleeve arms 664 suffices to rotate the sleeve 660 in the valve barrel 403G, without degrading the fluid seal therebetween.

The frictional engagement of the sleeve 660 with the suction valve barrel 403G and with the seal spool 662 frictionally maintains, against accidental displacement, the thus set circumferential position of the suction leak control sleeve 660 and hence the desired limited suction flow to the handpiece. At any time the user may again circumferentially displace a convenient one of the sleeve arms 674 to increase, decrease or shut off this partial, "leak", suction flow through the handpiece 206.

Figure 9A:
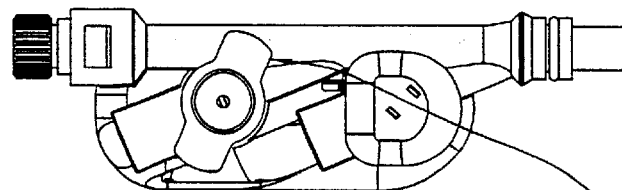
FIG. 9A is a view similar to FIG. 8A but with the suction leak sleeve in its open position.
Figure 9B:
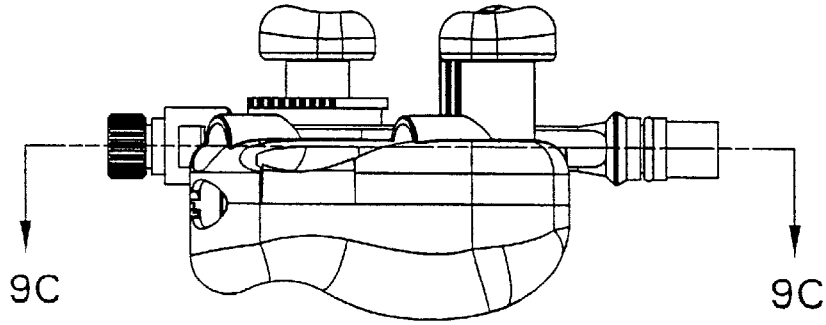
FIG. 9B is a view similar to FIG. 8B but with the suction leak sleeve in its open position.
Figure 9C:
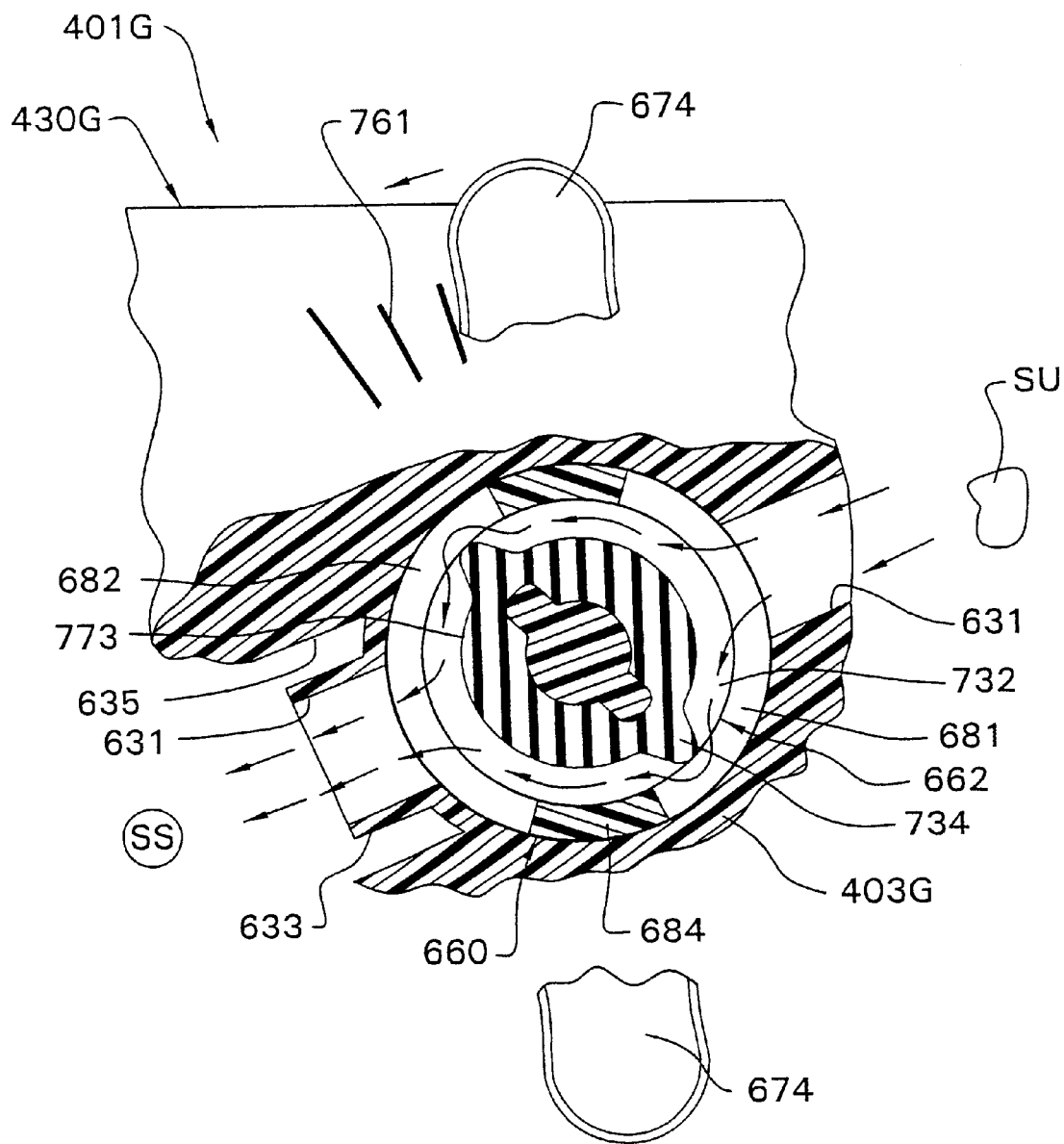
FIG. 9C is an enlarged, fragmentary, schematic sectional view substantially taken on the line 9C—9C of FIG. 9B.
Figure 10A:
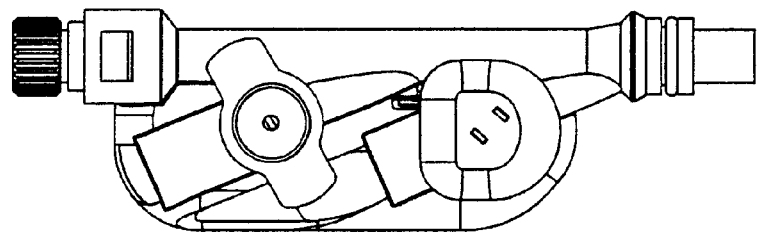
FIG. 10A is a view similar to FIG. 8A but with the suction valve in its full open position.
Figure 10B:
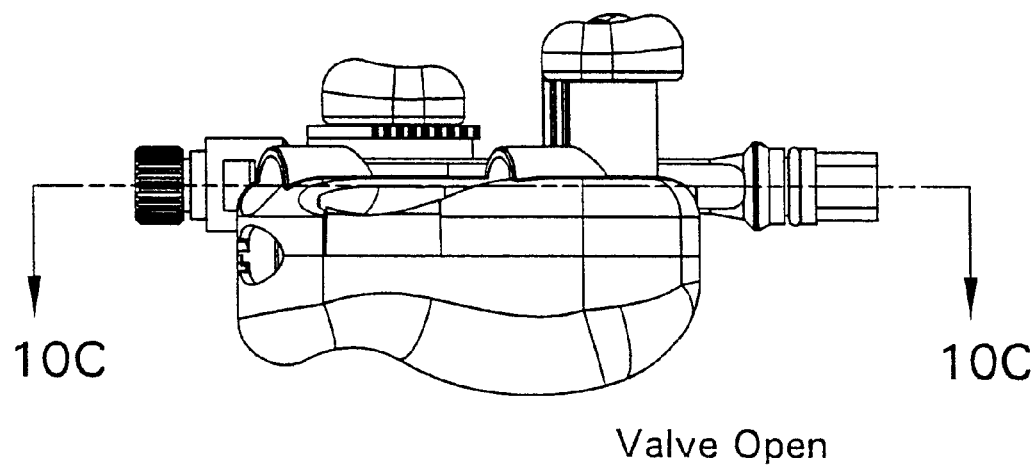
FIG. 10B is a view similar to FIG. 8B but with the suction valve in its full open position.
Figure 10C:
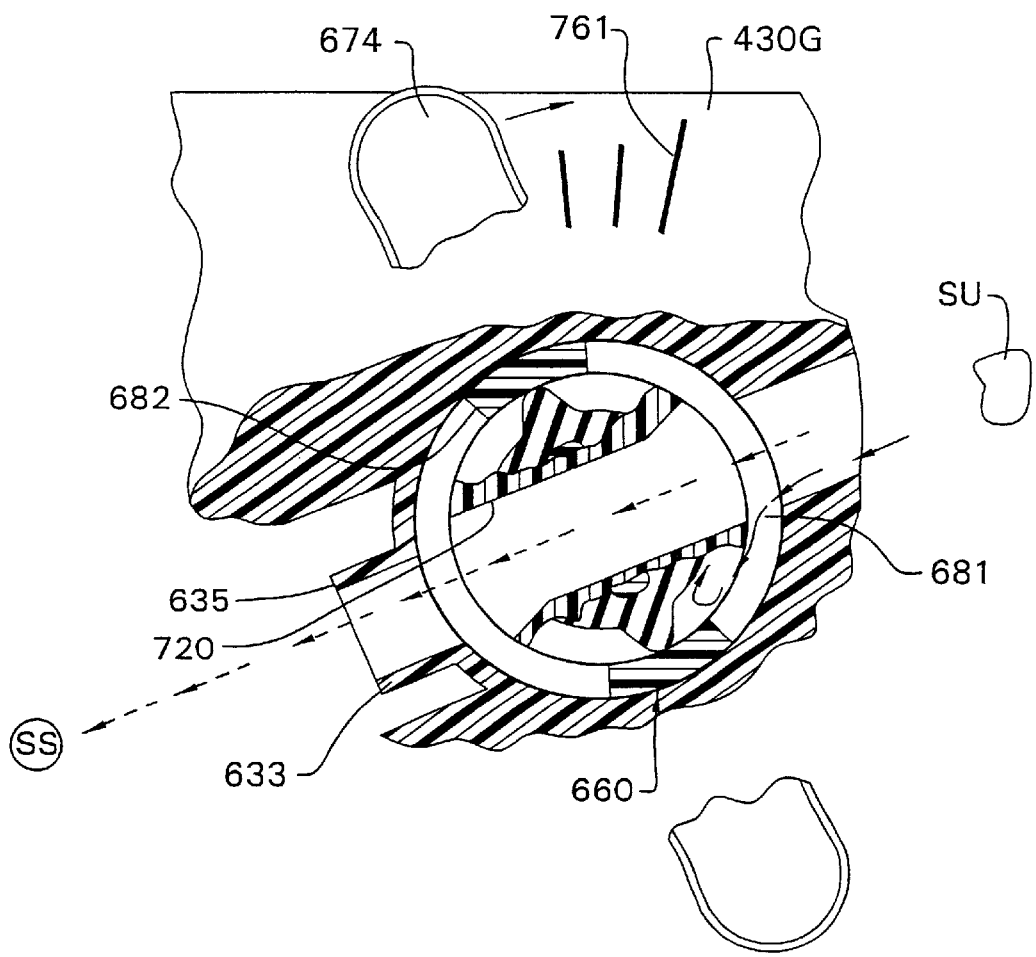
FIG. 10C is an enlarged fragmentary schematic cross sectional view substantially taken on the line 10C—10C of FIG. 10B with the suction leak sleeve in its closed position.
Figure 10D:
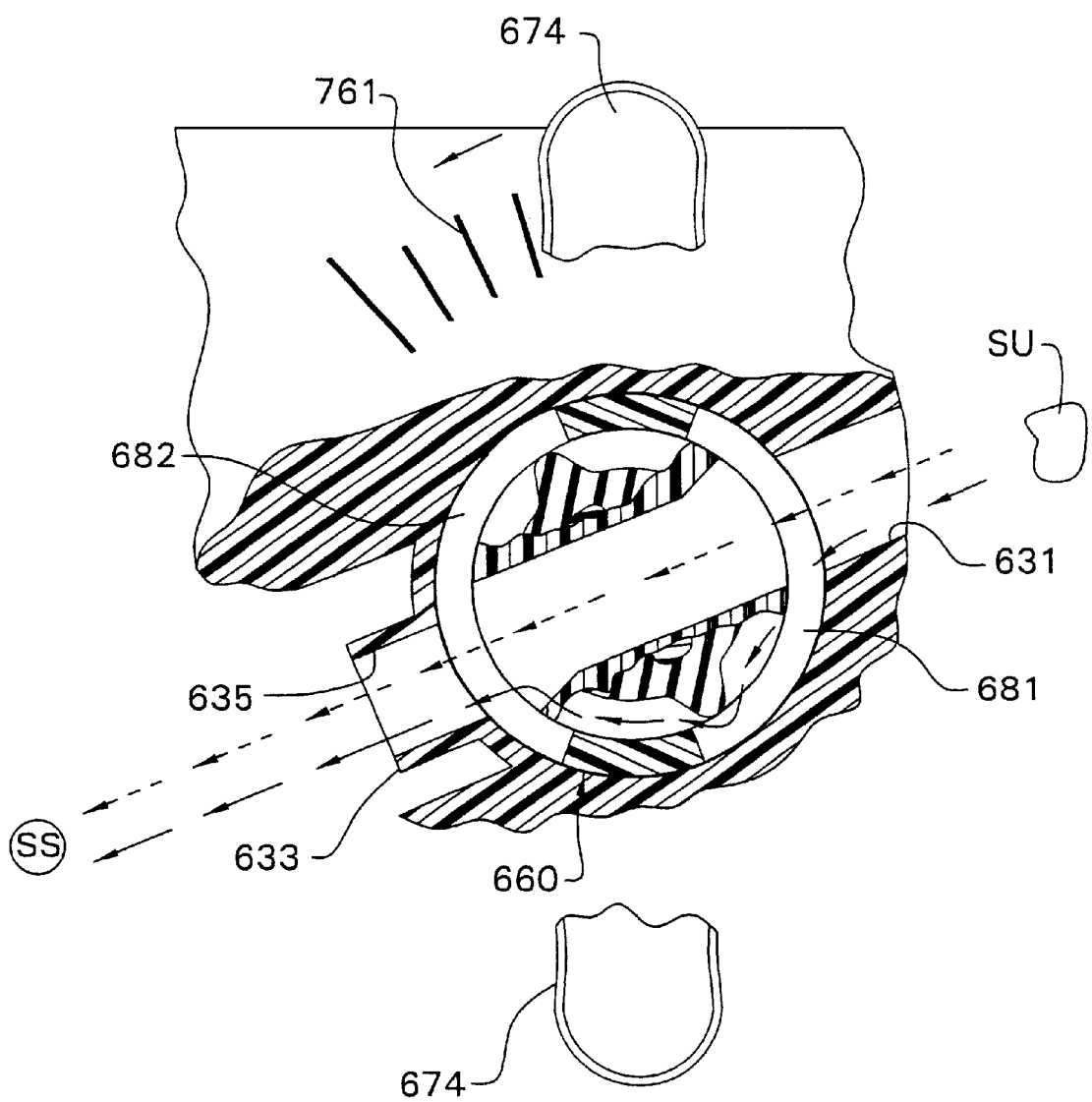
FIG. 10D is a view similar to FIG. 10C but with the suction leak sleeve in its open position.

In FIG. 9C, the arms of 674 are shown adjacent their clockwise-most (maximum suction leak) position, wherein the sleeve peripheral wall portions 684 are spaced counter-clockwise from the corresponding ribs 734 of the seal spool 662. The ribs 734 thus face the windows 681 and 682. However, the windows 681 and 682 are circumferentially long enough to still communicate with the suction through passage 631 of the handpiece top tub 401G. As a result, there is an open suction flow passage (as represented schematically by the arrows in FIG. 9C) through the front portion of the suction through passage 631, the sleeve window 681, the annular space between the interior of the sleeve 660 and the cylindrical midportion 733 of the seal spool 662, radially outward into the window 682, circumferentially in the window 682 around the exposed outer edges of the seal spool axial ribs 734, out the window 682 into the rearward portion of the suction through passage 631, through the nipple 633 and thus eventually to the suction source SS.

It will be seen from FIG. 9C that incremental counter-clockwise rotation of the seal spool 662 (with its arms 674) will incrementally narrow the portion of the windows 681 and 682 between the seal spool axial ribs 734 and the circumferentially advancing sleeve peripheral portions (indicated at 684). This incrementally reduces the cross-section of the leak suction flow path. That cross-section is reduced to zero and suction flow stops when the circumferentially advancing peripheral portions 684 engage and seal against the outer edges of the seal spool axial ribs 734, as in FIG. 8C above discussed.

The indent 683 (FIG. 4) in one window end cooperates with the outer edge of the adjacent seal spool axial rib 734 to allow very fine adjustment of suction leak level at very low suction leak levels, by more gradual reduction (or increase) of flow cross-section thereat, with the window 682 and the rest of the window 681 closed to suction flow.

Similarly, the indent 683 for a given sleeve rotation, makes more gradual the transition between no suction flow and least suction flow.

Thus, FIG. 9D schematically shows the more gradual increase in flow cross sectional flow area due to the indent 683 of the window 681 versus a hypothetical similar window 681' without the indent 683 (but with a semi-circular window end like other ends of the sleeve windows 681 and 682. More particularly, FIG. 9D shows several closely circumferentially spaced relative positions between the window 681 or 681' and the effective sealing edge of the seal spool rib 734 as the sleeve 660 is rotated to advance the leading end of the window 681 or 681'.

However, for convenience in illustration, FIG. 9D shows the several such relative positions by superposing several images of the sealing spool rib edge 734 on a single image of the advancing end of the window 681 or 681'. More particularly, the barely closed position of the window 681 or 681' is indicated at CL and several slightly, but successively increasingly open positions of the leading window end, relative to the rib 734, are indicated at OP1, OP2 and OP3 respectively. It will be seen at the FIG. 9D initial open position OP1, that the flow cross sectional area AR1 of the window 681, provided by the indent 683, is substantially less than the flow cross sectional area AR 1' provided by the generally circular end of the hypothetical window 681'. The same is true at successively assumed open positions OP2 and OP3 in FIG. 9D. Thus, the indent 683 provides more precise control of the magnitude of flow through the handpiece 26G at very low suction flow rates. Thus, the user can more precisely select the desired suction flow level in a narrow range of suction flows from very low down to zero. The user can thus, for example remove electrocautery smoke from the surgical site without risk of otherwise changing conditions in the surgical site.

It is possible to provide irrigation liquid flow to the surgical site by means of the irrigation liquid valve unit 650 (FIG. 2), hereafter discussed in more detail even with the suction valve unit push button 665 depressed (from normal suction flow) or with the suction leak control sleeve 660 rotated for suction leak flow. Typically, this may occur in the presence of a tip having separate suction and irrigation paths inserted through the conduit 430G and with the capability of separating, or sealing, from each other the portions of the tip communicating with the suction and irrigation valve units 651 and 650. An example is the suction pool tip shown in U.S. Pat. No. 5,827,218 assigned to the Assignee of the present invention.

Turning more specifically to the details of the irrigation valve unit 650 (FIG. 2), components generally corresponding to those above described with respect to the suction valve unit 651 will carry the same reference numerals with the suffix H added.

The irrigation valve unit 650 (FIG. 2) is assembled substantially in the manner above discussed with respect to the suction valve unit 651, except as follows.

Thus, the irrigation valve unit 650 (FIG. 2) includes a coil spring 661H, a seal spool 662H, a valve body 663H and an annular seal (e.g. O-ring) 664H preferably identical to the corresponding elements 661–664 of the suction valve unit 651. The irrigation valve unit 650 further includes a push button 690 which is generally similar to the push button 665 of the suction valve unit, except as noted hereafter.

The bore 454G of the irrigation valve barrel 402G is cylindrical (not tapered) and smaller in inside diameter than the suction valve barrel 403G, and indeed is similar in inside diameter to the suction leak control sleeve 660 (FIG. 2). Thus, the irrigation valve unit 650 includes no sleeve corresponding to the suction leak control sleeve 660 and the components 661H–664H fit snugly and slidably directly in the bore 454G of the irrigation valve barrel 402 with the annular seal (O-ring) 664H and the annular end flanges 732 (FIG. 6B) of the seal spool 662H sealingly bearing on the interior periphery of the suction valve bore 454G.

The opening and closing of the irrigation valve unit 650, by manual depression and release, respectively, of the push button 650 to pass or block, respectively, irrigation liquid flow through the irrigation throughpassage 630 (FIG. 3B) between the irrigation liquid source IL and the conduit 430G, is similar to that above described with respect to opening and closing, by depression and release, respectively, of the suction push button 665 (FIG. 2) to pass or block, respectively, suction flow through the suction throughpassage 631 (FIG. 3B) between the conduit 430G and suction source SS, and so needs no further comment.

Figure 15A:
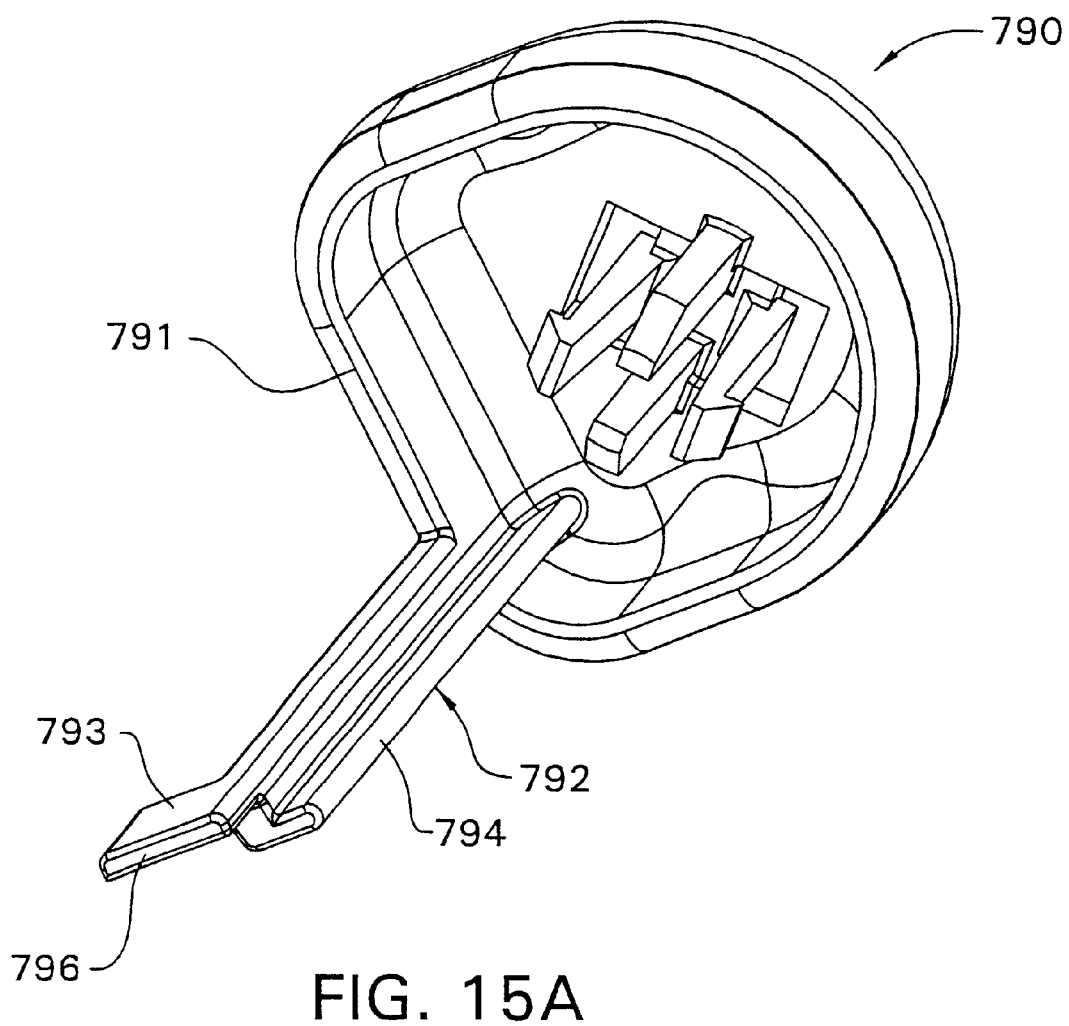
FIG. 15A is a bottom pictorial view of the irrigation pushbutton of the FIG. 1 handpiece.

The straight perimeter portion 791 of the irrigation push button 790 faces rearward (toward the suction valve unit) rather than forward toward the surgical site. In addition, the irrigation push button 790 has a depending, generally L-shaped cross section leg 792 integrally fixed (and preferably integrally molded) at the rear, left (seen looking forward, or rightward, in FIG. 2) corner of the push button 790. A generally rectangular, switch actuating foot 793 extends rearward from the bottom of the 792. The planes of the foot 793 and the front web 794 (FIG. 15A) of the leg 792 are offset to provide a generally Z-shaped cross section for the combined leg/foot 792, 793 as seen at the bottom 796 of the foot in FIG. 15A.

The top wall 410G (FIG. 3A) of the top tub 401G is perforated by a substantially Z-shaped hole 800 located adjacent the conduit 430G, the suction duct front portion 627, and the irrigation duct rear portion 624. The Z-shaped hole 800 (FIG. 3A) is located, sized and shaped to snugly but smoothly slidably receive the leg 792 and foot 793 downwardly therethrough. The leg 792 and its foot 793, pass down through hole 800 in the inverted top tub 401G as the valve body 663H passes down into the valve barrel 402G. Thus, in the installed, normally closed, upper position (FIG. 1) of the irrigation valve unit 650 the foot 793 is spaced between the top wall 410G of the top tub 401G and the bottom of the front, irrigation liquid, valve barrel 402G (FIG. 2).

A pair of switch carrier plates 413G (FIGS. 3J and 15B–D) and a further pair of switch carrier plates 414G depend from the top wall 410G into the downward opening cavity 410G of the inverted top tub 401G. The plates 413G and 414G are parallel to each other and preferably parallel to the length axes of the valve barrels 402G and 403G. The plates 413G and 414G are spaced inboard from the side edges of the top tub 401G. The plate pairs 413G and 414G are spaced apart on opposite sides of the common diametral plane of the valve barrels 402G and 403G. Relatively narrow switch mounting gaps 420G and 421G laterally space apart the respective paired plates 413G, 413G and pair plates 414G, 414G. The parallel plates 413G extend rearward to and are fixed to the peripheral wall of the suction valve barrel 403G and extend forward toward the hole 800. Indeed, the outboard plate 413G has an extension portion 801 extending forward the length of the rear arm 802 of the Z-shaped hole 800 and flanking the outboard edge thereof.

An electrical switch SWG (FIGS. 2 and 15B–D) comprises a pair of switch elements 510G and 511G of electrically conductive springy sheet metal, such as copper or a suitable alloy.

The switch element 510G comprises a base plate 512G with gripper tabs 513G acutely angled with respect thereto. The switch element 510G further includes an electric connector terminal 514G and a switch contact leaf 515G. The switch element 511G is of somewhat different shape, but includes a base plate 520G including gripper tabs 521G acutely angled with respect thereto, and an electric connector terminal 522G and switch contact leaf 523G extending therefrom.

The switch element 510G is fixed in the interior of the inverted tub 401G as follows. The base plate 512G is slidably inserted upward (in the orientation of FIGS. 2 and 15D) into the switch mounting gap 421G between the depending switch carrier plates 414G. The gripping tabs 513G enter and become jammed in the switch mounting gap 421G to prevent the switch element 510G from accidentally leaving its operative position of FIGS. 15B and D, within the inverted tub 501G. This leaves the electrical connector terminal 514G and switch contact leaf 515G outside the switch mounting gap 421G. The electrical connector terminal 514G thus lies between the outboard switch carrier plate 414G and the opposed sidewall of the inverted tub 401G. The switch contact leaf 515G is resiliently self-urged toward the switch carrier plates 413G as more fully discussed hereafter.

The base plate 520G of the switch element 511G is inserted upward into the switch mounting gap 420G (FIG. 15D) and is frictionally fixed therein by engagement of the gripping tabs 521G with the opposed inboard switch carrier plate 413G. The electrical connector terminal 522G is disposed between the outboard switch carrier plate 413G and the adjacent other inverted tub sidewall adjacent the bottom of the outboard sidewall 413G. The switch contact leaf 523G extends upward along the outboard switch carrier plate 413G within the switch mounting gap 420G and into electrical contact with the switch contact leaf 515G of the switch element 510G to complete an electrical connection between the two switch elements 510G and 511G.

It is convenient to install the switch elements 510G and 511G on their corresponding switch carrier plate pairs 413G and 414G with the irrigation valve unit 650 installed in the handpiece and its push button 790 and foot 793 depressed, to thereby facilitate proper location of the switch contact leaves 515G and 523G on opposite sides of the foot 793.

The tubes 23G and 33G are sealingly slipped over their corresponding nipples 632 and 633 (FIGS. 3B) in a fixed manner (as by press fit) and are lead from the top tub 401G through their respective recesses 634 and 635 and respective communicating hole 640 and notch 641. The cable 27G, which piggybacks the irrigation tube 23G, exits with it through the hole 640 as generally indicated in FIG. 1.

As in the incorporated-by-reference application, the pump unit 10G (FIG. 1) preferably comprises a pump P driven by a motor M connected in circuit with a battery pack B and conductors 103G of a single pair electric cable 27G piggybacked on the irrigation supply tube 23G leading to the handpiece 26G.

The wires 103G, suitable insulated, terminate within the inverted tub 401G in conventional connectors 525G (FIG. 15B) compatible with the electrical connector terminals 514G and 522G, respectively. In the preferred embodiment shown, the connectors 525G are of resilient female type telescopingly fixable on the electrical connector terminals 514G and 522G. In this way, the FIG. 15B electrical contact between the leaf 515G and leaf 523G closes the switch SWG, which energizes the pump motor M from the battery B.

Figure 11A:
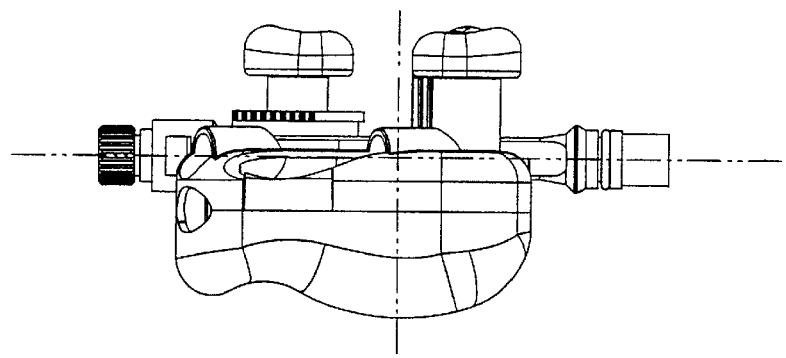
FIG. 11A is a view generally similar to FIG. 8B and wherein the irrigation valve is in its full closed position.

With the irrigation push button 790 in its upper, rest position shown in FIGS. 1, 11A and 16A, the dimetrical through passage 630H is upperwardly displaced from and sealed from the irrigation through passage 630. The foot 793 (FIG. 15D) is thus in its uppermost position schematically indicated at 793' where it bends the switch contact leaf 515G to its dotted line position 515G' spaced from the other switch contact leaf 523G such that the switch SWG is in its open, nonconductive condition and the pump P (FIG. 1) is not energized. Because of the closed position of the irrigation valve unit 650, there is no irrigation liquid flow through the handpiece 26G.

Figure 12A:
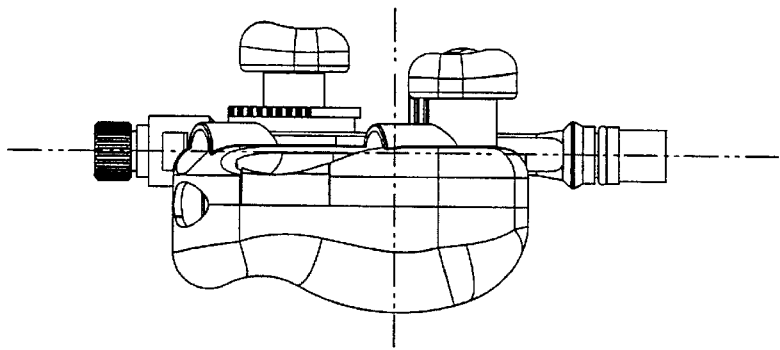
FIG. 12A is a view similar to FIG. 11A but showing the irrigation valve in a partially closed condition.
Figure 13A:
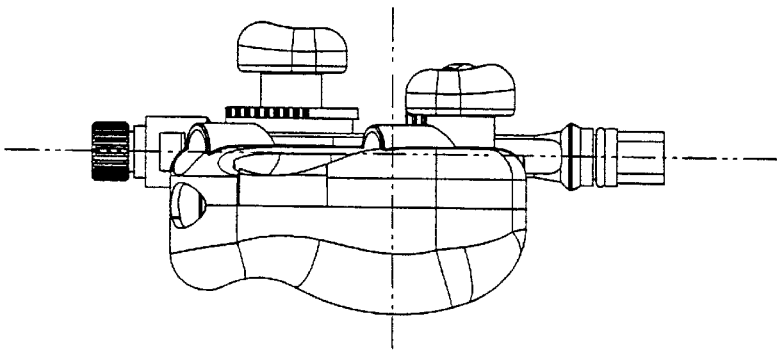
FIG. 13A is a view similar to FIG. 11A but showing the irrigation valve in its fully open position.

Partial depression of the irrigation push button 790, as seen in FIGS. 12A and 16B, brings the irrigation dimetral through passage 720H to partially register with the irrigation throughpassage 630 to provide a fractional flow cross section. Partial depression of the irrigation push button partially depresses the foot 793 (FIGS. 15B–D) and permits the switch contact leaf 515G to spring further rightward wherein its free end is closer to but not yet in contact with the switch contact leaf 523G. Thus, the switch SWG is still open and the pump P (FIG. 1) is still not energized. The pump P is of a type (e.g. a rotating vane pump as in the incorporated-by-reference application) which permits gravity flow of irrigation liquid therethrough when deactuated. Thus, the partial opening of the irrigation valve unit 650 allows gravity flow of irrigation liquid from the irrigation liquid source IL through the chamber of the at-rest pump P, tube 23G, partially open handpiece irrigation valve unit 650, the front end portion 431G of the conduit 430G and thence onward to the surgical site SU, given that the irrigation liquid source IL is, as usual, at a height above that of the handpiece 26G. This provides for a relatively low, gentle flow of irrigation liquid through the handpiece to the surgical site SU, which flow can readily be modulated by movement of the push button 790, foot 793 and irrigation valve body 663H within a range of intermediate positions from closed to (in the preferred embodiment shown) about ⅓ open. The foot 793 is shown about ⅓ depressed at 793" in FIG. 15D.

Figure 15B:
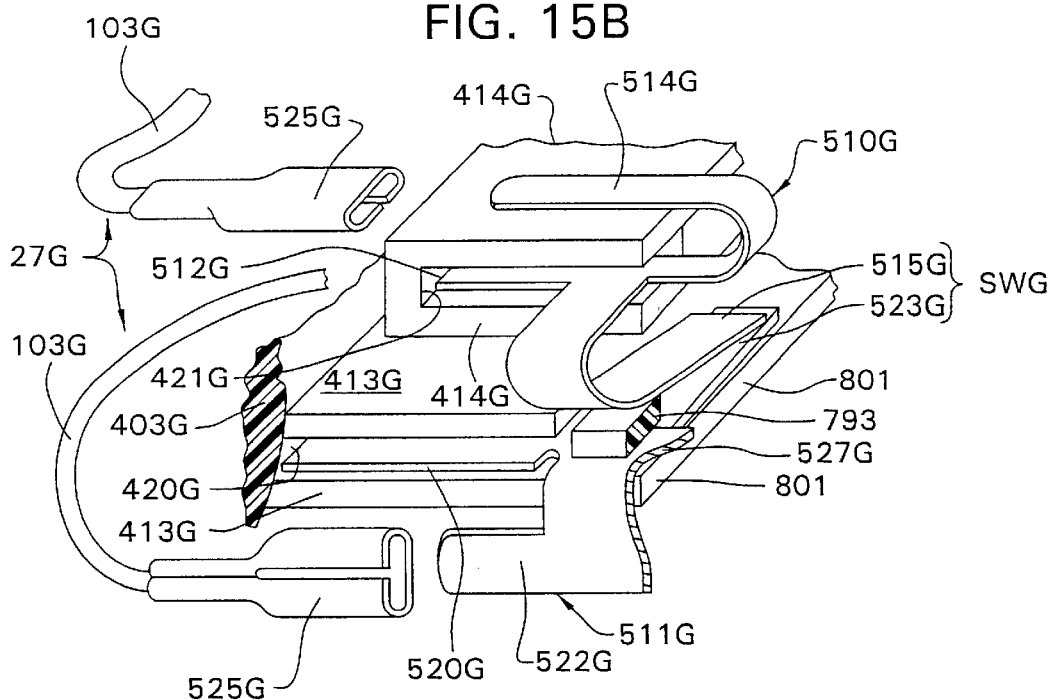
FIG. 15B is a fragmentary pictorial view of the FIG. 2 switch elements installed in the top tub of the FIG. 2 handpiece, looking generally upward and rearward in the FIGS. 1 and 2 orientation of the handpiece, and showing the switch element mounting area of FIGS. 3F and 3J.
Figure 15C:
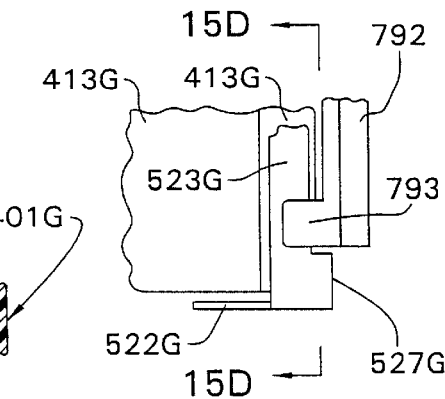
FIG. 15C is a fragmentary schematic view taken generally on the line 15C—15C of FIG. 3F and showing the switch actuator foot in an intermediate position with respect to one of the FIG. 2 switch elements.
Figure 15D:
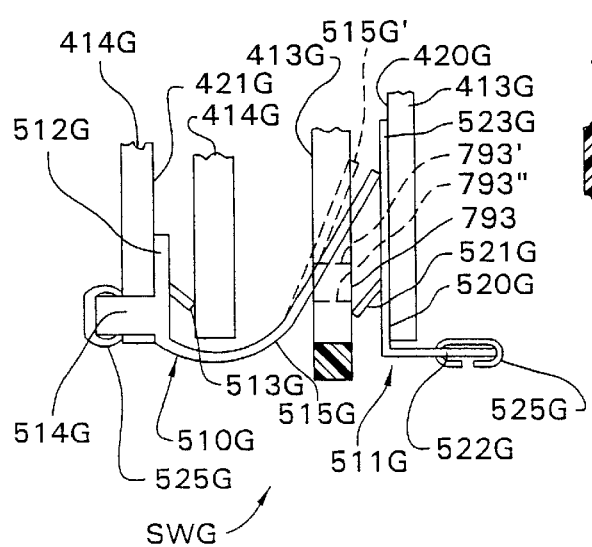
FIG. 15D is a schematic sectional view substantially taken on the line 15D—15D of FIG. 15C and showing alternate positions of the switch actuator foot and switch elements, including open, intermediate and closed positions.

With slightly further depression, the foot 793 moves out of contact with the switch contact leaf 515G and allows the latter to spring into contact the switch leaf contact 523G, thereby closing the switch SWG (see FIGS. 15B and D). This through the conductors 103G of the cable 27G thereby closes the circuit of the motor M to the battery B, electrically energizes the motor M from the battery B, and activates the pump P. This condition continues as the pushbutton 790 is depressed through the last portion, e.g. ⅔ of its range.

Also, depression of the irrigation push button 790 (FIG. 16C), and thus of the irrigation valve body 663H, through such last portion e.g. ⅔ of their range progressively further opens the latter's diametrical through passage 720H to the irrigation through passage 630, and so progressively further opens the irrigation valve unit 650. Thus, in this part of the range of opening of the irrigation valve unit 650, the activated pump P adds its force to the above mentioned gravitational force, to maximize the pressure of irrigation liquid applied to the irrigation valve unit 630 to the handpiece 26G and thus the extent of opening of irrigation valve unit 650 controls the rate of pumped irrigation flow therethrough to the surgical site SU.

Maximum flow rate occurs with the valve unit 650 fully open.

In contrast, in handpieces produced in accord with the incorporated-by-reference application, depression of the irrigation valve pushbutton first actuated the pump and only thereafter began to open the valve, thus providing no possibility of gravity flow of irrigation liquid through the handpiece.

To complete assembly of the handpiece, the downward opening top tub 401G is placed on the upward opening bottom tub 610, such that the pins 611 of the former enter the corresponding sockets 612 of the latter, thereby seating the top tub 401G firmly on the bottom tub 610 in the matter shown in FIG. 1. In the embodiment shown, the lower edge of the top tub 401G includes an inset lip 810 (FIG. 2) which rests snugly in the stepped rim 811 of the lower tub 610. The installation of the upper tub 401G on the bottom tub 610 can be made permanent by interposition of a suitable adhesive between the pins 611 and socket 612 or/and between the inset lip 810 and stepped rim 811.

Figure 8C:
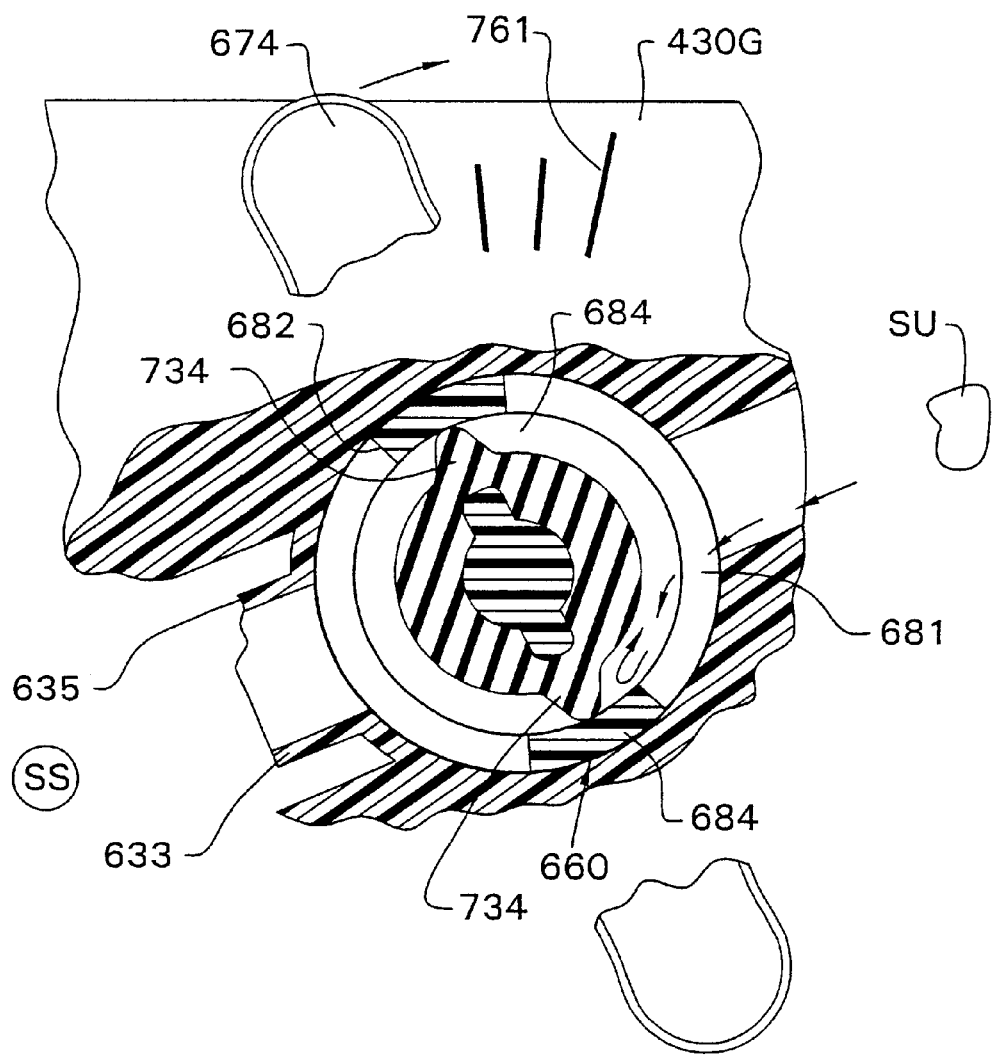
FIG. 8C is an enlarged, fragmentary, schematic sectional view substantially taken on the line 8C—8C of FIG. 8B.

The rear end of the conduit 430G is normally sealingly closed by the plug 440G (FIG. 2), here with its O-ring 442G and adapter 620. With the O-ring 437G installed on the conduit front end portion 431, any desired tip TP (FIG. 1) can be installed in the front end of the conduit 430G. If desired, the rear end of the conduit 430G can be left open to enable insertion through the conduit 430G to a surgical site, any desired elongate tool, e.g. a conventional electrocautery tool (not shown). The internal threads of the conduit rear portion 432 allows threaded, sealed installation of such a tool, which tool may extract through the conduit 430G and through a suitable hollow tip TP to enable the tool to work tissue at the surgical site SU, while yet permitting valved irrigation (gravity or pumped), valved suction, or adjustable constant leak (or by-pass) suction (as for smoke evacuation during electrocautery tissue working), namely by respectively, partial or full depression of the irrigation valve push button 790, depression to the desired extent of the suction valve push button 665 or/and appropriate angular setting of the suction leak control sleeve by means of its arms 674 (FIGS. 8C and 9C).

The ergonomically rounded, easily gripped shelf 400G (FIGS. 17A–D) has a convexly rounded front end 820, a preferably convexly rounded rear end 821 from which the tubes 23G and 33G extend generally rearwardly, generally at the angle of the suction duct rear portion 626 to the conduit 430G. The housing 400G has a bottom wall 822 (FIG. 17A) having a convexly rounded front part 823 and a rear part defining a transverse groove 824 extending from side-to-side across the bottom wall 822.

The shape of the handpiece 26G facilitates comfortable, secure holding and convenient operation by the hand H (FIGS. 17B and 17C) of a user.

For example, in FIG. 17B, the user's hand H holds the handpiece 26G in what may be referred to as an "overhand" position. Here the convexly rounded, bottom wall, front part 823 is shaped to complement the cupped palm 836 of the user's hand H and the bottom wall transverse groove 824 is shaped to complement the web joining the thumb 830 and first finger 831 of the user's hand H. The elongate conduit 403G is shaped and located in complement to the joinder of the fingers and palm of the user's hand. The suction pushbutton 651 and irrigation pushbutton 790 thus are conveniently positioned under the tips of the first finger 831 and middle or third fingers 832 or 833 of the user's hand, for easy depression and release thereby, with such fingers in the somewhat clenched positions shown in FIG. 17B. The protruding front end of the conduit 430G and the upstanding irrigation valve barrel 402G define therebetween a notch 834 adapted to receive the little finger 835 of the user's hand H. The handpiece 26G is thus securely gripped in the user's hand H by the thumb 831, palm 836 and little finger 835, leaving the fingers 831–833 free to manipulate the pushbuttons 665 and 790. The arms 674 of the suction leak control sleeve are adjacent the first finger 831 and thumb 830 of the user's hand for rotation by either or both as desired.

As a further example and alternative, FIG. 17C shows what may be referred to as an "underhand" position for holding and manipulating the handpiece 26G. Here, the handpiece 26G rests in the hand H of the user adjacent the joint of the fingers to the palm with the first finger 831 disposed in the notch 837 defined by the front end of the conduit 430G and the front end 831 of the shell 400G, the index finger 832 engaging the convexly curved front bottom wall portion 823, the third finger 833 disposed in the transverse groove 824 of the bottom wall, and the little finger 834 disposed in the notch 838 (FIG. 17A) formed between the rear end 821 and tube 23G. This leaves the thumb 830 free to adjust the position of the arm 674 and depress the pushbuttons 665 and 790.

The handpiece 26G may be otherwise positioned in the user's hand H, but the FIG. 17B and FIG. 17C positions illustrate how the shape of the shell 400G, and the overall arrangement of above discussed parts of the handpiece 26G, facilitate gripping and manipulation of the handpiece 26G by the hand H of a user.

Parts of the apparatus above described are preferably of molded, substantially rigid, plastics material of conventional type, except as otherwise described, e.g. the switch elements 510G and 511G of electrically conductive springy metal, and annular seals 473G and 482G and 486G of conventional resilient rubberlike material, and wires 103D and connectors 525 of electrically conductive metal, and suction leak control sleeve 660 of a resilient self-lubricating material such as polyethylene.

Although a particular preferred embodiment of the invention has been disclosed in detail for illustrative purposes, it will be recognized that variations or modifications of the disclosed apparatus, including the rearrangement of parts, lie within the scope of the present invention.

What is claimed is:

1. A surgical suction irrigation handpiece comprising:
   a housing shell of rounded elongate shape having a first end, a second end, a first elongate wall extending between and rounded into said ends, said first elongate wall having a convexly rounded part adjacent said first end and a transverse groove between and rounded into said second end and said convexly rounded part, said shell further having a second elongate wall opposite said first elongate wall and extending between said ends;
   an elongate conduit extending beyond said first end of said shell and integrally fixed with respect to said shell adjacent a length edge of said second elongate wall;
   at least one fluid tube extending away from said shell adjacent said second end;
   manual valve actuators facing out from and spaced along said elongate second wall adjacent said conduit and including a first said valve actuator located substantially opposite and facing away from said convexly rounded part of said first elongate wall and a second said manual valve actuator located substantially opposite to said transverse groove in such first elongate wall.

2. The apparatus of claim 1 in which at least one said manual valve actuator is supported for translation on an axis extending into said housing shell, an arm rotatably fixed about said translation axis and radially extending therefrom, said arm being substantially opposite said transverse groove and extending generally sidewardly from said translation axis, said arm constituting a third manual valve actuator.

3. The apparatus of claim 1 in which said first shell end is convexly rounded and said conduit extends beyond said rounded shell first end and defines therewith a finger engagable notch.

4. The apparatus of claim 1 in which said shell second end is convexly rounded and said one fluid tube extends from said rounded second end, said one tube and rounded housing second end forming a finger engagable notch.

5. The apparatus of claim 1 in which said shell has elongate side walls circumferentially connecting said first and second elongate walls and longitudinally extending between said ends, ends of said transverse groove being convexly rounded into said sidewalls.

6. The apparatus of claim 5 in which said transverse groove and sidewalls form a surface complementary to a thumb/first finger web of an adult user's hand, said convexly rounded part of said first elongate wall forms a surface complementary to the cupped palm of an adult user's hand, said transverse groove and convexly rounded part of said first elongate wall being circumferentially spaced from said manual valve actuators to facilitate their engagement by an adult user's middle fingers, said second elongate wall and said first end having a rounded joinder, said manual valve actuator adjacent said first end having a valve barrel extending beyond said second elongate wall, said conduit extending beyond said first end with said valve barrel forming a finger receiving notch at said rounded joinder, said manual valve actuator adjacent said second end having a translation axis extending into said shell, an arm extending radially from said transverse axis and generally sidewardly of said housing shell, said arm being within reach of and engagable by at least one of the thumb and first finger of an adult user's hand.

7. The apparatus of claim 5 in which said transverse groove and sidewalls form a surface complementary to a middle finger of an adult user hand, said convexly rounded part of said first elongate wall and adjacent sidewalls form a surface complementary to a further finger of an adult user hand, said conduit extending beyond said first end of said shell and therewith defining a notch engagable by a further finger of a user hand, said tube and second end forming a notch engagable by a further finger of a user hand, said manual valve actuators being circumferentially spaced from said second elongate wall to facilitate their engagement by the thumb of an adult user's hand, said manual valve actuator adjacent said second end having a translation axis extending into said shell, an arm extending radially from said translation axis and generally sidewardly of said housing shell and being within reach of and engagable by the thumb of an adult user's hand.

8. A surgical suction irrigation handpiece, comprising:
   a housing including a fluid flow passage and a valve barrel transversely interposed in said fluid flow passage, said fluid flow passage opening into said valve barrel,
   said valve barrel having an open end and a closed end, a structure in said closed end including a transverse slot;
   a valve body coaxially reciprocable in said valve barrel, said valve body having a transverse through passage, said valve body having a springy leg slidable axially in and held against rotation by said transverse slot to prevent said valve body from rotating in said valve barrel, said leg having a foot and resiliently holding said foot trapped under an edge of said transverse slot to prevent escape of said valve body from said valve barrel open end.

9. The apparatus of claim 8 in which said valve body has two said springy legs resiliently engaging opposite ends of said slot.

10. The apparatus of claim 8 in which said valve body has an actuable end remote from said leg and adjacent said open end of said valve barrel, said valve body actuable end having a transverse recess, said valve body having a transverse through opening at the inner end of said recess, a pushbutton having a hand engagable outboard face and an inboard extending springy leg insertable in said transverse recess to prevent rotation of said pushbutton on said valve body, said pushbutton leg having a foot and resiliently holding said foot in said transverse through opening to prevent removal of said pushbutton from said valve body.

11. The apparatus of claim 8 in which said structure in said closed end of said valve barrel includes an interiorly extending coaxial boss, said slot being in the interior end of said boss, a transversely wider second slot opening through said valve barrel closed end and aligned with said first mentioned slot to receive said foot and an adjacent portion of said leg freely reciprocably therethrough with said valve body at an inboard position in said valve barrel, a spring in said valve barrel backed by said valve barrel closed end and surrounding said boss and leg and bearing on a portion of said valve body from which said leg extends to urge said valve body toward the open end of said valve barrel.

12. The apparatus of claim 8 in which said valve body has a reduced diameter waist having a reduced diameter, longitudinally extending, generally cylindrical core, a seal spool having a coaxial through passage snugly sleeved on said waist, an axially extending groove and seal rib connecting and positively preventing relative rotation of said seal spool and valve body such that said body transverse through passage and seal rib are circumferentially fixed with respect to each other, said seal pool having coaxial radially outwardly extending circular end flanges of generally rounded profile which flank a substantially cylindrical mid-portion of reduced diameter, said seal rib protruding radially outwardly from said mid-portion and axially between said flanges.

13. The apparatus of claim 12 including a leak control sleeve radially interposed between said valve body and the interior wall of said valve barrel, said sleeve having a circumferentially extending window open to said housing fluid flow passage at one side of said valve barrel and to said valve body, said valve body having an inboard position in said valve barrel and communicating said valve body transverse through passage through said sleeve window with said housing fluid flow passage, said valve body having an outboard position in said valve barrel and communicating said seal spool through said window with said housing fluid flow passage, said leak control sleeve having a closed circumferential position in which said seal rib bears sealingly on the interior face of said leak control sleeve at a location circumferentially beyond the end of said window so as to block flow circumferentially therepast, said sleeve having a further circumferential position in which said seal rib faces said window at a location circumferentially spaced from the ends of said window so as to open a flow path including (1) said housing fluid flow passage on one side of said valve barrel, (2) an end portion of said window radially opposed thereto, (3) the intermediate portion of said window radially between said seal rib and the interior wall of said valve barrel, (4) the other end portion of said window, and (5) a circumferentially extending path lying radially between another portion of said reduced diameter mid-portion of said seal spool and the interior wall of said sleeve.

14. The apparatus of claim 13 in which the axially spaced end flanges of said seal spool seal against the interior wall of said sleeve at locations axially flanking the axially spaced edges of said window to prevent leakage axially therebeyond and toward the ends of said valve body.

15. The apparatus of claim 14 including a circumferentially extending ridge on the interior wall of the said valve barrel adjacent the closed end thereof, said sleeve having a radially outwardly projecting rim snap fitted past said ridge, said sleeve having a radially outward projecting flange bearing on the outer end of said valve barrel, said sleeve being axially fixed with respect to said valve barrel by said rim and flange thereof.

16. The apparatus of claim 13 in which the outer end of said valve barrel has a circumferentially extending notch therein, said sleeve having a radially outwardly extending flange which circumferentially rides on the outer end of said valve barrel, a radially outwardly extending key fixed with respect to said sleeve adjacent said flange and the outer periphery of said sleeve, said key being circumferentially narrower than and disposed in said notch, said key and notch limiting circumferential displacement of said sleeve window with respect to said housing fluid flow passage and seal rib.

17. The apparatus of claim 16 including a user hand engageable arm fixedly radially outwardly extending from said flange and said valve barrel for arcuate movement of said sleeve with respect to said valve barrel and valve body, said housing carrying angularly spaced indicia along the path of arcuate movement of said arm to indicate the circumferential position of said sleeve window and thus the extent of leakage around said seal rib.

18. The apparatus of claim 8 in which said fluid flow passage is a suction passage.

19. The apparatus of claim 12 in which said housing fluid flow passage is an irrigation liquid passage and said valve barrel is of inside diameter to snugly receive said valve body for axial movement therein, said seal spool having at least one annular sealing flange bearing in sealing engagement on the interior wall of said valve body axially inboard of said irrigation flow passage.

20. The apparatus of claim 12 in which said housing has two said valve barrels, namely a suction valve barrel and an irrigation valve barrel, and two such fluid flow passages, namely, a suction flow passage intercepted by said suction valve barrel and an irrigation flow passage intercepted by said irrigation valve barrel, two said valve bodies being received respectively in said suction and irrigation valve barrels, the inner diameter of said suction valve barrel being greater than that of said irrigation valve barrel, and a suction leak control sleeve disposed radially between said suction valve barrel and said one of said valve bodies therein.

21. The apparatus of claim 13 in which the interior wall of said valve barrel tapers divergently toward said valve barrel open end, said leak control sleeve having an outer peripheral wall which tapers in a manner complementary to said valve barrel interior wall taper, such tapers providing a rotating seal between said sleeve and valve barrel and thereby sealing the edges of said window against leakage.

22. A surgical fluid flow controlling handpiece having a range of relatively low flow rates and a relatively high flow rate, comprising:
   a housing having a fluid flow passage therethrough;
   first flow control means on said housing and displaceable through a range of positions to change the flow rate through said fluid flow passage over a range of relatively low flow rates;
   second flow control means on said housing and associated with said first means and operable, with said first means at a given location in its said range of positions, to provide a relatively high flow rate.

23. The apparatus of claim 22 in which said second flow control means comprises a valve member axially displaceable in said housing and located across said fluid flow passage, said valve member having a transverse opening, said transverse opening being in registry with said fluid flow passage to provide said relatively high flow rate, said axially displaceable valve member having a seal adjacent said transverse opening, said first flow control means comprising a rotatable further member in said housing surrounding said valve member, said range of positions being a range of circumferential positions of said rotatable further member with respect to said housing and valve member, said rotatable further member having a wall, said wall being interposed between said valve member seal and said fluid flow passage at said one end of said range, said rotatable further member having a window interposed between said seal and said fluid flow passage at positions in said range and offset from said one end of said range, said offset positions corresponding to different positions of said window open to said seal and fluid flow passage, and thus to said range of relatively low flow rates.

24. The apparatus of claim 22 in which said first flow control means comprise an axially displaceable valve member located in said housing and across said fluid flow passage, said valve member having a transverse opening displaceable through said range of positions with respect to said fluid flow passage, in which said valve means transverse opening is substantially fully open to said fluid flow passage at substantially one end of said range and is substantially fully closed to said fluid flow passage at the other end of said range and is correspondingly variously partly open to said fluid flow passage at intermediate parts of said range, said fluid flow passage having a relatively low flow rate fluid supply connection, said second flow control means comprising normally open switch contacts on said housing and operatively associated with said valve member, said normally open condition of said switch contacts corresponding to a first part of said range of valve member positions excluding said full open position of said valve member, an electric circuit including said contacts and an energy source and a fluid pump unit connected to said fluid supply connection, said switch contacts having a closed position corresponding to a second part of range of valve positions including said full open end of said range of positions of said valve member and to an energized condition of said fluid pump unit wherein it supplies a relatively high fluid flow rate.

25. A surgical fluid flow handpiece comprising:
   a housing having a fluid through passage;
   a valve barrel interposed in said fluid through passage;
   a leak control sleeve rotatable in said valve barrel, said sleeve having a peripheral wall and a window through part of said peripheral wall, said sleeve having at least one circumferential position communicating said window and housing fluid through passage;
   a valve member axially displaceable in said sleeve and having a substantially closed position;
   a seal spool on said valve member and having an axially extending, radially protruding rib, said seal spool sharing a common radial plane of said valve barrel with said housing fluid through passage and sleeve window with said valve member in said closed position;
   said sleeve having a closed circumferential position sealing said sleeve peripheral wall against said seal spool axial rib and thereby blocking flow through said housing fluid through passage, said sleeve having a substantially fully open circumferential position opposing said seal spool rib to a circumferentially intermediate part of said window and thus opening a flow path (1) circumferentially through said window and (2) around said rib and (3) between parts of said housing fluid through passage separated by said valve barrel, said window having axially spaced substantially parallel circumferentially extending edges and a circumferential end portion in which said circumferentially extending edges converge and form a circumferentially elongated, tapered indent, such that successive increments of circumferential opening of said sleeve, from said closed circumferential position toward said fully open circumferential position, include (1) an axially narrow flow opening past said axial rib and (2) successive incrementally axially wider flow openings, to facilitate precise selection of flow rate in a relatively narrow band of flow rates at the low end of the range of flow rates permitted by relative positioning of said rib with respect to said window.

26. The apparatus of claim 25 wherein said substantially parallel circumferential edges lie in axially spaced first and second substantially radial planes of said sleeve, said tapered indent having one circumferential edge continued in said first radial plane and its other circumferential edge angled from said second radial plane toward said first radial plane.

27. The apparatus of claim 26 in which said tapered indent has a rounded end of diameter less than half of the axial width of said window.

28. The apparatus of claim 25 in which said seal spool has diametrically opposite ones of said axially extending ribs, said sleeve having a further window circumferentially spaced from and on the opposite side of said sleeve from said first mentioned window, said windows being open to parts of said housing fluid through passage separated by said valve barrel, said windows together including three relatively blunt circumferential end portions and a tapered end portion defined by said tapered indent, said tapered end portion making said first mentioned window longer than said second window, such that said first mentioned spool rib starts to open said tapered end of said first mentioned window while the other said rib is still circumferentially spaced between said windows, such that the said flow rates at the low end of the range are precisely controlled by the circumferential location of said first mentioned rib along said window tapered end portion.

29. The apparatus of claim 28 wherein the maximum leak flow rate around said seal spool corresponds to a location of said ribs circumferentially along said respective said windows at a maximum distance from said ends of said respective windows.

30. A surgical fluid flow apparatus comprising:
   a housing having a fluid flow path therethrough;
   a first valve structure in said fluid flow path and having a first variable size valve opening;
   a first variable manual control member operatively connected to said variable size valve opening, said first valve structure including a valve member movable in said housing along a path across a portion of said fluid flow path to vary the size of said variable size valve opening, said valve member having positions on said path corresponding to a (1) fully closed position, (2) a range of partially closed positions and (3) a substantially fully open position;
   a switch actuating member movable on said housing and operatively fixed with respect to said valve member for movement therewith;
   a switch fixed with respect to said housing along the path of movement of said switch actuating member and having an electric current flow condition corresponding to said valve member positions from intermediate in said range to said fully open position and an electric current blocking condition corresponding to said valve member fully closed position and to said position intermediate in said range of partially closed positions.

31. The apparatus of claim 30 in which said valve structure comprises a valve member axially moveable into said housing and having a transverse opening axially movable across said housing fluid flow path to define said variable size valve opening therewith, said switch being located in said housing adjacent an axially intermediate, partly open position of said valve member.

32. The apparatus of claim 31 in which said switch comprises a fixed conductive leaf, a springy conductive leaf self-pressed against said fixed leaf in the electric current flow condition of said switch, said leaves extending substantially parallel to said valve member path and being mounted on said housing adjacent the inboard end of said valve member path and extending along said valve member path, said switch actuator member comprising an nonconductive foot fixed with respect to said valve member for travel therewith, said foot being slidable between said leaves and separating said leaves throughout about the first ⅓ of the opening travel of said valve member and allowing contact between said leaves in about the last ⅔ of said opening travel.

33. The apparatus of claim 30 including an elongate fluid path connected between said housing fluid flow path and a fluid port having, in use, a relatively gentle pressure level corresponding to a relatively small pressure differential from atmospheric pressure, a pump unit locatable remotely with respect to said handpiece and connected in said elongate fluid path adjacent said fluid port and having parts respectively operatively connected to said handpiece and said fluid port, said pump unit having a deactuated condition in which it is a passive portion of said fluid path and said handpiece connected part of said pump unit is substantially at said relatively gentle pressure level, said pump unit having an actuated condition providing a pressure increase across said pump unit and in which the handpiece connected part of said pump unit is at a relatively aggressive pressure level corresponding to a relatively large pressure differential from atmospheric pressure, an electric circuit connecting such switch and said pump unit and an electric power source, such that said electric current flow position of said switch corresponds to said pump unit actuated condition, whereby, in use, said pump unit (1) passes said relatively gentle fluid pressure level to said handpiece with said variable size valve opening in said fully and adjacent ones of said partially closed positions and (2) applies said relatively aggressive fluid pressure level to said handpiece with said variable size valve opening in said substantially fully open and adjacent ones of said partially closed positions.

34. The apparatus of claim 33 in which said fluid flow path is an irrigation liquid flow path.

35. The apparatus of claim 34 in which said irrigation liquid flow path includes an irrigation liquid source locatable above said handpiece to apply a gravity responsive positive pressure to liquid it supplies to said pump unit, said pump unit in its energized condition applying to its handpiece connected part a pressure greater than said gravity responsive pressure.

36. A surgical fluid flow apparatus comprising a handpiece;
a gravity liquid supply;
a pump unit operatively connecting said gravity liquid supply to said handpiece, said pump having an off condition in which it is a conduit to supply liquid at gravity pressure to said handpiece, said pump unit having an on condition in which it adds further pressure to said liquid and thus supplies liquid to said handpiece at higher than gravity pressure;
a valve structure in said handpiece controlling liquid flow through said handpiece to a surgical site, said valve structure including a pump on/pump off control operatively connected to said pump unit, said valve structure having partially and fully closed positions corresponding to said off condition of said pump unit and to gravitational pressure liquid applied to said handpiece, said valve structure having partially and full open positions corresponding to said on condition of said pump unit and to greater than gravitational liquid pressure in said handpiece.

37. The apparatus of claim 36 in which said pump unit comprises a motor responsive to said pump on/pump off control of said handpiece, a pump in driven relation with said motor, said pump comprising a pumping chamber and a liquid impelling member disposed in said pumping chamber, said pumping chamber having a wall, said gravity liquid supply comprising a hollow inlet element fixed on said wall of said pumping chamber and opening therethrough into said pumping chamber.

38. The apparatus of claim 37 in which said hollow inlet element comprises a hollow tubular spike fixedly upstanding from said pumping chamber wall and having a surface engagable in an outlet of a conventional irrigation liquid supply bag.

39. The apparatus of claim 36 including a liquid path through said handpiece, and in which said valve structure in said handpiece comprises a valve chamber interposed in said liquid path through said handpiece and a valve element reciprocable over a range of locations in said valve chamber and having one position opening and a second position closing said liquid path through said handpiece, said pump on/pump off control comprising a control element reciprocable with said valve element over at least a part of said range of locations of said valve element, said pump on/pump off control further including an elongate control path operatively connecting said handpiece and pump unit and responsive to a displacement of said control element for turning on said motor.

40. The apparatus of claim 36 in which said pump on/pump off control comprises (1) a motor and (2) an electric switch and (3) an electrical conductor connecting said switch to said pump unit and connected in circuit with said motor.

41. The apparatus of claim 36 in which said handpiece includes a valve chamber, said valve structure including a valve piston reciprocable in said valve chamber, said pump on/pump off control comprising a switch having a first part coupled to said valve piston and movable in a first direction along a path, said switch having a second part disposed along said path, said valve piston having an intermediate position corresponding to a closed, conductive condition of said switch.

42. A surgical fluid flow controlling handpiece comprising:
a housing having a fluid flow passage with a surgical site opposable port;
an irrigation liquid connection to said housing and an irrigation valve between said irrigation connection and said fluid flow passage, said irrigation valve having an open position communicating said irrigation connection to said said fluid flow passage;
a suction connection to said housing and a suction valve between said suction connection and said fluid flow passage, said suction valve having an open position communicating said suction connection to said fluid flow passage;
a member associated with said suction valve and having a position corresponding to a limited suction flow between said suction connection and fluid flow passage.

* * * * *

UNITED STATES PATENT AND TRADEMARK OFFICE
CERTIFICATE OF CORRECTION

PATENT NO.    : 6,652,488 B1
DATED         : November 25, 2003
INVENTOR(S)   : Reid Cover et al.

It is certified that error appears in the above-identified patent and that said Letters Patent is hereby corrected as shown below:

Column 19,
Line 25, replace "pool" with -- spool --.

Column 24,
Line 56, delete "said" (second occurence).

Signed and Sealed this

Twenty-fifth Day of May, 2004

JON W. DUDAS
*Acting Director of the United States Patent and Trademark Office*